United States Patent
Weichert et al.

(10) Patent No.: US 12,109,256 B2
(45) Date of Patent: *Oct. 8, 2024

(54) RADIOHALOGENATED AGENTS FOR IN SITU IMMUNE MODULATED CANCER VACCINATION

(71) Applicant: Wisconsin Alumni Research Foundation, Madison, WI (US)

(72) Inventors: Jamey Weichert, Sun Prairie, WI (US); Paul M. Sondel, Madison, WI (US); Anatoly Pinchuk, Fitchburg, WI (US); Zachary Morris, Madison, WI (US); Mario Otto, Fitchburg, WI (US); Bryan Bednarz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 912 days.

This patent is subject to a terminal disclaimer.

(21) Appl. No.: 16/919,191

(22) Filed: Jul. 2, 2020

(65) Prior Publication Data

US 2020/0330567 A1    Oct. 22, 2020

Related U.S. Application Data

(63) Continuation of application No. 15/652,400, filed on Jul. 18, 2017, now Pat. No. 10,736,949.

(60) Provisional application No. 62/363,608, filed on Jul. 18, 2016.

(51) Int. Cl.
*A61K 39/00* (2006.01)
*A61K 39/39* (2006.01)
*A61K 39/395* (2006.01)
*A61K 51/04* (2006.01)

(52) U.S. Cl.
CPC ........ *A61K 39/001* (2013.01); *A61K 39/0011* (2013.01); *A61K 39/39* (2013.01); *A61K 39/39558* (2013.01); *A61K 51/0408* (2013.01); *A61K 51/041* (2013.01); *A61K 51/0489* (2013.01); *A61K 2039/505* (2013.01); *A61K 2039/53* (2013.01); *A61K 2039/545* (2013.01); *A61K 2039/55511* (2013.01); *A61K 2039/55533* (2013.01); *A61K 2039/572* (2013.01); *A61K 2039/58* (2013.01); *A61K 2039/585* (2013.01)

(58) Field of Classification Search
CPC ............................ A61P 35/04; A61K 51/0408
See application file for complete search history.

(56) References Cited

U.S. PATENT DOCUMENTS

| | | |
|---|---|---|
| 8,535,641 B2 | 9/2013 | Weichert |
| 2010/0316567 A1 | 12/2010 | Weichert |
| 2014/0171627 A1 | 6/2014 | Bhushan |
| 2015/0030538 A1 | 1/2015 | Weichert et al. |
| 2018/0126012 A1 | 5/2018 | Weichert |

FOREIGN PATENT DOCUMENTS

| | | |
|---|---|---|
| WO | 2005/084716 A2 | 9/2005 |
| WO | 2007/013894 A2 | 2/2007 |
| WO | 2009/027706 A2 | 3/2009 |
| WO | 2010/144788 A2 | 12/2010 |
| WO | 2016/081203 A2 | 5/2016 |
| WO | 2016/207732 A1 | 12/2016 |
| WO | 2017/025496 A1 | 2/2017 |
| WO | 2017/079535 A1 | 5/2017 |
| WO | 2018/017526 A1 | 1/2018 |
| WO | 2018/022571 A1 | 2/2018 |

OTHER PUBLICATIONS

Pierce et al (Human Vaccine & Immunotherapeutics, 2015, vol. 11, pp. 1901-1909) (Year: 2015).*
Toth et al, VirchowsArchiv A Pathol anat, 1990, vol. 417, pp. 273-276 (Year: 1990).*
Basarn et al, AJR, 2005, vol. 184, pp. 1103-1110 (Year: 2005).*
Davorak, American Journal of Pathology, 2003, vol. 162, 1747-1747, (Year: 2003).*
Brechbiel et al., "Bifunctional Chelates for Metal Nuclides" Q J Nucl Med Mol Imaging, HHS Public Access Author manuscript; available in PMC, pp. 1-17, PMCID: PMC2693392, (Jun. 9, 2009).
Cai et al., "Chelators for copper radionuclides in positron emission tomography radiopharmaceuticals", J. Label Compd. Radiopharm, 57(4):224-230, (Apr. 2014).
Engeland et al., "CTLA-2 and PD-L1 checkpoint blockade enhances oncolytic measles virus therapy", Molecular Therapy, 22(11):1949-1959, (Nov. 2014).
Esposito et al., "Immune checkpoint inhibitors with radiotherapy and locoregional treatment: synergism and potential clinical implications", Current Opinion in Oncology, 27(6):445-451, (Oct. 2015).

(Continued)

*Primary Examiner* — Karen A. Canella
(74) *Attorney, Agent, or Firm* — McDonnell Boehnen Hulbert & Berghoff LLP

(57) ABSTRACT

A method of treating a malignant solid tumor in a subject is disclosed herein. The method includes the steps of administering to the subject an immunomodulatory dose of a radiohalogenated compound that is differentially taken up by and retained within malignant solid tumor tissue, and performing in situ tumor vaccination in the subject by intratumorally injecting into (or treating via a separate method) at least one of the malignant solid tumors a composition that includes one or more agents capable of stimulating specific immune cells within the tumor microenvironment. In certain exemplary embodiments, the radiohalogenated compound has the formula:

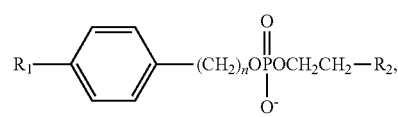

wherein $R_1$ is a radioactive halogen isotope, n is 18 and $R_2$ is $-N^+(CH_3)_3$.

18 Claims, 27 Drawing Sheets

(56) References Cited

OTHER PUBLICATIONS

Fong L: "A phase Ib trial to study the safety and tolerability of atezolizumab with radium-223 dichloride in patients with metastatic castrate resistant prostate cancer (mCRPC)", Cancer Research 20170701 American Association for Cancer Research Inc. NLD, vol. 77, No. 13, Supplement I, Jul. 1, 2017 (Jul. 1, 2017), XP55560570, ISSN: 1538-7445.

Fonge et al., "Influence of formulation variables on the biodistribution of multifunctional block copolymer micelles", Journal of Control Release, 157(3):366-374, (Feb. 2012).

Gao et al., "Enhanced anti-tumor efficacy through a combination of integrin αvβ6-targeted photodynamic therapy and immune checkpoint inhibition", Theranostics, 6(5):627-637, (Mar. 2016).

Hernandez et al., "Combination of targeted radionuclide therapy and checkpoint blockade augments therapeutic response in a syngeneic murine model of melanoma", Journal of Nuclear Medicine, 59(1):119, (May 2018).

Hicks, "Use of molecular targeted agents for the diagnosis, staging and therapy of neuroendocrine malignancy", Cancer Imaging, 10(1A):S83-S91, (Sep. 2010).

Hu et al., "Pm-149 DOTA bombesin analogs for potential radiotherapy: in vivo comparison with Sm-153 and Lu-177 labled DO3A-amide-βAla-BBN(7-14)NH2", Nuclear Medicine and Biology, 29:423-430, (2002).

Johnson et al., "Radiofrequency ablation combined with KS-IL2 immunocytokine (EMD 273006) results in an enhanced antitumor effect against murine colon adenocarcinoma", Clinical Cancer Research, 15(15):4875-4884, (Aug. 2009).

Koumarianou et al., "Comparative study on DOTA-derivatized bombesin analog labled with 90Y and 177Lu: in vitro and in vivo evaluation", Nuclear Medicine and Biology, 36(6):591-603, (Aug. 2009).

Li et al., "Aminocarboxylate complexes and octreotide complexes with no carrier added 177Lu, 166Ho and 149Pm", Nuclear Medicine and Biology, 30(3):241-251, (Apr. 2003).

Lyseng-Williamson et al., "Ipilimumab: a guide to its use in advanced melanoma", American Journal of Clinical Dermatology, 13(5):349-354, (Oct. 2012).

Malamas et al., "Sublethal exposure to alpha radiation (223Ra dichloride) enhances various carcinoma' sensitivity to lysis by antigen-specific cytotoxic T lymphocytes through calreticulin-mediated immunogenic modulation", Oncotarget, 7(52):86937-86947, (Dec. 2016).

Mohsin et al., "Radiolanthanide-labeled monoclonal antibody CC49 for radioimmunotherapy of cancer: biological comparison of DOTA conjugates and 149Pm, 166Ho, and 177Lu", Bioconjugate Chemistry, 17(2):485-492, (Feb. 2006).

Monsieurs et al., "Patient dosimetry for 131I-MIBG therapy for neuroendocrine tumours based on 123I-MIBG scans", European Journal of Nuclear Medicine and Molecular Imaging, 29(12):1581-1587, (Oct. 2002).

Morris et al., "In Situ tumor vaccination by combining local radiation and tumor-specific antibody for immunocytokine treatments", Cancer Research, 76(13):3929-3941, (Jul. 2016).

Pardoll et al., "The blockade of immune checkpoints in cancer immunotherapy", Nature Reviews, 12:252-264, (Mar. 2012).

Pilones et al., "Combination of radiotherapy and immune checkpoint inhibitors", Seminars in Radiation Oncology, 25(1):28-33, (Jan. 2015).

Postow et al., "Immune checkpoint blockade in cancer therapy", Journal of Clinical Oncology, 33(17):1974-1982, (Jun. 2015).

Storkus W., "Combination treatment of VLA-4 targeted radionuclide therapy and immunotherapy of metastatic melanoma", Molecular imaging and biology, 19(1) (S419) Supplement 1, (Sep. 2017).

Swart et al., "Combination Approaches with Immune-Checkpoint Blockade in Cancer Therapy", Frontiers in Oncology, 6(1):233, (Nov. 2016).

Weichert, Jamey P., et al., "Alkylphosphocholine Analogs for Broad-Spectrum Cancer Imaging and Therapy," Science Translational Medicine, 6(240):1-10, (Jun. 11, 2014).

International Search Report and Written Opinion, mailed Mar. 13, 2019, International Patent Application No. PCT/US2018/059927.

Cascini et al., "124 Iodine: A Longer-Life Positron Emitter Isotope—New Opportunities in Molecular Imaging", BioMed Research International, 2014, 9 pages.

Phan et al., "The diagnostic value of 124I-PET in patients with differentiated thyroid cancer", Eur. J. Nucl. Med. Mol. Imaging, 2008, vol. 35, 958-965.

* cited by examiner

RADIOHALOGENATED AGENTS FOR IN SITU IMMUNE MODULATED CANCER VACCINATION

CROSS-REFERENCE TO RELATED APPLICATIONS

This application is a continuation of U.S. application Ser. No. 15/652,400 filed on Jul. 18, 2017, which claims the benefit of U.S. provisional Application No. 62/363,608 filed on Jul. 18, 2016. Each of these applications is incorporated by reference herein in its entirety.

STATEMENT REGARDING FEDERALLY SPONSORED RESEARCH OR DEVELOPMENT

This invention was made with government support under CA197078 awarded by the National Institutes of Health. The government has certain rights in the invention.

FIELD OF THE DISCLOSURE

This disclosure relates generally to methods of treating cancer. In particular, the disclosure is directed to methods of treating a cancer comprising one or more malignant solid tumors in a subject by (a) systemically administering to the subject an immunomodulatory dose of a radioiodinated compound that is differentially taken up by and retained within solid tumor tissue, and (b) performing in situ tumor vaccination in the subject at one of the malignant solid tumors using one or more treatments capable of stimulating specific immune cells within the tumor microenvironment.

BACKGROUND

Current cancer treatment typically involves systemic chemotherapy whereby non-targeted small molecule or antibody directed cytotoxic agents preferentially enter, or bind to (in the case of antibody directed agents) and kill cancer cells by a variety of mechanisms. External beam radiation therapy (xRT), which is often combined with chemotherapy, kills cancer cells by inducing nuclear DNA double strand breaks resulting in cell-cycle death. Unlike systemic chemotherapy, xRT depends on the ability to accurately determine the anatomic location of the tumor. Surgical resection of tumors also depends on the ability to see the tumor and on complete removal, since residual tumor cells will quickly reestablish the tumor following surgery. Surgery and xRT are generally limited to the local treatment of malignant tumors and thus are limited in treating disseminated or metastatic disease, which is why chemotherapy is often used in conjunction with these treatment modalities. Although systemic chemotherapy is capable of reaching many distant metastatic sites, with the possible exception of brain metastases, for all too many patients, responses are typically short-lived (months to several years) and ultimately result in tumor recurrence.

Because the body's natural immune system is also capable of destroying cancer cells following their recognition, immunologic approaches are rapidly becoming more prevalent in cancer treatment paradigms. However, some cancer cells, and to a greater extent cancer stem cells, manage to initially avoid immune-surveillance and actually acquire the ability to evolve and ultimately survive by remaining relatively immune invisible [Gaipi et al, Immunotherapy 6:597-610, 2014].

One specific immunologic approach that is being increasingly investigated is "in situ vaccination," a strategy that seeks to enhance tumor immunogenicity, generate tumor infiltrating lymphocytes (TIL) and drive a systemic anti-tumor immune response directed against "unvaccinated," disseminated tumors. In in situ vaccination, a malignant solid tumor is injected with (or treated with) one or more agents that facilitate the release of tumor antigens while simultaneously providing pro-inflammatory signals to reverse the immune-tolerizing microenvironment of the tumor [Pierce et al, Human Vaccines & Immunotherapoeutics 11(8):1901-1909, 2015; Marabelle et al, Clin. Cancer Res. 20(7):1747-56, 2014; Morris et al, Cancer Research, e-pub ahead of print, 2016]. Although recent data from clinical trials and pre-clinical models illustrate the potential of such an approach, there is a great need in the art for in-situ vaccination methods exhibiting improved systemic efficacy.

Radiation hormesis is a decades-old hypothesis that low doses of ionizing RT can be beneficial by stimulating the activation of natural protective repair mechanisms that are not activated in the absence of ionizing RT [Cameron and Moulder, Med. Phys. 25:1407, 1998]. The reserve repair mechanisms are hypothesized to be sufficiently effective when stimulated as to not only cancel the detrimental effects of ionizing RT but also inhibit disease not related to RT exposure. Perhaps related, the abscopal effect is a phenomenon reported in the 1950's, whereby, xRT treatment of one tumor actually causes shrinkage of another tumor outside the RT treatment area. Although rare, this phenomenon is thought to be dependent on activation of the immune system. Together, hormesis and the abscopal effect support the potential interaction and stimulation of the immune system by low dosage (immune stimulatory but non-cytotoxic) RT, which may then be combined with other immunologic approaches, such as in situ vaccination.

We have previously published that the combination of local xRT+in situ vaccination are potently synergistic in treating large established tumors in mice, when there is a single tumor present [Morris et al, Cancer Research, e-pub ahead of print, 2016]. We have surprisingly discovered (and disclose herein) that the combination of in situ vaccination and xRT does not result in inhibited tumor growth in the presence of a second, non-radiated tumor. Apparently, the non-radiated tumor exhibits a dampening effect (which we have designated as "concomitant immune tolerance") on the immunomodulatory effect of the xRT and in situ vaccine on the radiated tumor. This concomitant immune tolerance can be overcome, enabling efficacy of in situ vaccination, when xRT is given to all areas of tumor. However, xRT cannot be effectively used in combination with in situ vaccination methods in the presence of multiple tumors, particularly if the tumors are not few in number, or if the location of one or more of the tumors is not precisely known, or if it is not feasible to deliver xRT to all sites of tumor. Accordingly, in combination with in situ vaccination, there is a need for improved methods of delivering an immunomodulatory dose of RT to all tumors within a subject, regardless of their number and anatomic location.

BRIEF SUMMARY

We have previously shown that certain alkylphosphocholine analogs are preferentially taken up and retained by malignant solid tumor cells. In U.S. Patent Publication No. 2014/0030187, which is incorporated by reference herein in its entirety, Weichert et al. disclose using analogs of the base compound 18-(p-iodophenyl)octadecyl phosphocholine (NM404; see FIG. 1) for detecting and locating, as well as for treating, a variety of malignant solid tumors. If the iodo moiety is an imaging-optimized radionuclide, such as iodine-124 ($[^{124}I]$-NM404), the analog can be used in positron emission tomography-computed tomography (PET/CT) or single-photon emission computed tomography (SPECT) imaging of solid tumors. Alternatively, if the iodo moiety is a radionuclide optimized for delivering therapeutic doses of RT to the solid tumors cells in which the analog is taken up, such as iodine-125 or iodine-131 ($[^{125}I]$-NM404 or $[^{131}I]$-NM404), the analog can be used to treat the solid tumors.

Such analogs not only target a wide variety of solid tumor types in vivo, but also undergo prolonged selective retention in tumor cells, thus affording high potential as radiotherapy agents. Moreover, tumor uptake is limited to malignant cancer and not premalignant or benign lesions. Thus, such agents are well suited for delivering a sub-cytotoxic but immunomodulatory dose of ionizing RT to all malignant tumors present within a subject, regardless of whether their number and locations are known.

Accordingly, in a first aspect, the disclosure encompasses a method of treating a cancer comprising one or more malignant solid tumors in a subject. The method includes the steps of: (a) administering to the subject an immunomodulatory dose of a radiohalogenated compound that is differentially taken up by and retained within malignant solid tumor tissue; and (b) performing in situ tumor vaccination in the subject at one or more of the malignant solid tumors using one or more treatments capable of stimulating specific immune cells within the tumor microenvironment. An "immunomodulatory dose" is a low or sub-cytotoxic RT dose of the targeted radiotherapy agent. Although NM404 is used in the examples below, the targeted radiotherapy agent could be any targeted radiohalogenated therapy agent that include alpha, beta, auger, and/or gamma emitters, including, without limitation, radioiodinated metaiodobenzylguanidine (MIBG). The key feature is that targeted radiotherapy agent emits low or sub-cytotoxic RT doses that are not lethal to either the cancer cells or the relevant immune cells.

In some embodiments, the one or more treatments capable of stimulating specific immune cells can include xRT. In some embodiments, the one or more treatments capable of stimulating specific immune cells include intratumorally injecting into at least one of the malignant solid tumors a composition that includes one or more agents capable of stimulating specific immune cells within the tumor microenvironment. In some embodiments, the one or more agents capable of stimulating specific immune cells can include an immunostimulatory monoclonal antibody (mAb), a pattern recognition receptor agonist, an immunostimulatory cytokine, an immune stimulatory nanoparticle, an oncolytic virus, or any combinations thereof. Non-limiting examples of immunostimulatory monoclonal antibodies that could be used include anti-GD2 antibodies, anti-CTLA-4 antibodies, anti-CD137 antibodies, anti-CD134 antibodies, anti-PD-1 antibodies, anti-KIR antibodies, anti-LAG-3 antibodies, anti-PD-L1 antibodies, anti-CD40 antibodies, or combinations thereof. In some embodiments, the immunostimulatory mAb is an antibody to a tumor-specific antigen. In some embodiments, the composition that includes one or more immunostimulatory monoclonal antibodies may also include interleukin-2 (IL-2). In some embodiments, the anti-GD2 mAb that is used may include hu14.18, and optionally, may further include IL-2 (i.e., a fusion protein of the two).

In some embodiments, the immunostimulatory cytokine is IL-2, interleukin-12 (IL-12), interleukin-15 (IL-15), interleukin-21 (IL-21), or an interferon (IFN).

In some embodiments, the pattern recognition receptor agonist is an agonist of a toll-like receptor (TLR). Non-limiting examples of such TLRs TLR include TLR-1, TLR-2, TLR-3, TLR-4, TLR-5, TLR-6, TLR-7, TLR-8, TLR-9, or TLR-10.

In some embodiments, the radiohalogenated compound is metaiodobenzylguanidine (MIBG), wherein the iodine atom is a radioactive iodine isotope. In some embodiments, the radioactive iodine isotope is $^{123}I$, $^{124}I$, $^{125}I$ or $^{131}I$.

In some embodiments, the radiohalogenated compound has the formula:

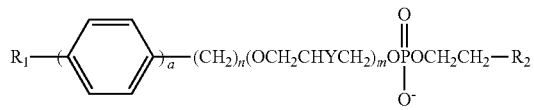

or a salt thereof. $R_1$ is or includes a radioactive halogenated isotope, a is 0 or 1, n is an integer from 12 to 30, m is 0 or 1, Y is —H, —OH, —COH, —COOX, —OX, or —OCOX, wherein X is an alkyl or an arylalkyl, and $R_2$ is —$N^+H_3$, —$N^+H_2Z$, —$N^+HZ_2$, or —$N^+Z_3$, wherein each Z is independently an alkyl or an aryl.

In some embodiments, the radioactive halogen isotope is a radioactive isotope of iodine, bromine, or astatine. In some such embodiments, the radioactive halogen isotope is $^{211}I$, $^{123}I$, $^{124}I$, $^{125}I$ or $^{131}I$. In some such embodiments, the radioactive halogen isotope is $^{125}I$ or $^{131}I$. In some such embodiments, the radioactive halogen isotope is $^{131}I$.

In some embodiments, a is 1 and m is 0. In some embodiments, n is 18. In some embodiments, $R_2$ is —$N^+H_3$.

In some embodiments, a is 1, m is 0, n is 18, and $R_2$ is —$N^+H_3$. In some such embodiments, the radioactive halogen isotope is $^{211}I$, $^{123}I$, $^{124}I$, $^{125}I$ or $^{131}I$ (the compound is [$^{211}As$]-NM404, [$^{123}I$]-NM404, [$^{124}I$]-NM404, [$^{125}I$]-NM404 or [$^{131}I$]-NM404).

In some embodiments, the radio-halogenated compound is administered intravenously.

In some embodiments, the subject is a human.

In some embodiments, the method optionally includes the step of exposing one of the malignant solid tumors to xRT.

In some embodiments, the method optionally includes the step of determining the immunomodulatory dose of the radiohalogenated compound. In some such embodiments, this step is performed by administering to the subject a detection-facilitating dose of the radiohalogenated compound, and subsequently detecting signals originating from the one or more malignant solid tumors within the subject that are characteristic of the radioactive halogen isotope within the radiohalogenated compound. In some such embodiments, the radioactive halogen isotope contained in the radiohalogenated compound used in the detection-facilitating dose is $^{211}I$, $^{123}I$, $^{124}I$, $^{125}I$ or $^{131}I$. A non-limiting exemplary radiohalogenated compound that could be used is [$^{124}I$]-NM404. In some such embodiments, the immunomodulatory dose of the radiohalogenated compound is calculated from the strength of the signals originating from the one or more malignant solid tumors within the subject. Optionally, the step of detecting signals characteristic of the radioactive halogen isotope is performed by positron emission tomography (PET) imaging or single-photon emission computed tomography (SPECT) imaging.

Non-limiting examples of the cancers presenting as malignant solid tumors that could treated using the disclosed method include melanoma, neuroblastoma, lung cancer, adrenal cancer, colon cancer, colorectal cancer, ovarian cancer, prostate cancer, liver cancer, subcutaneous cancer, squamous cell of the skin or head and neck, intestinal cancer, cervical cancer, glioma, breast cancer, pancreatic cancer, soft tissue sarcomas, Ewings sarcoma, rhabdomyosarcoma, osteosarcoma, retinoblastoma, Wilms' tumor, and pediatric brain tumors.

Other objects, features and advantages of the present invention will become apparent after review of the specification, claims and drawings.

DETAILED DESCRIPTION

I. In General

Figure 1:
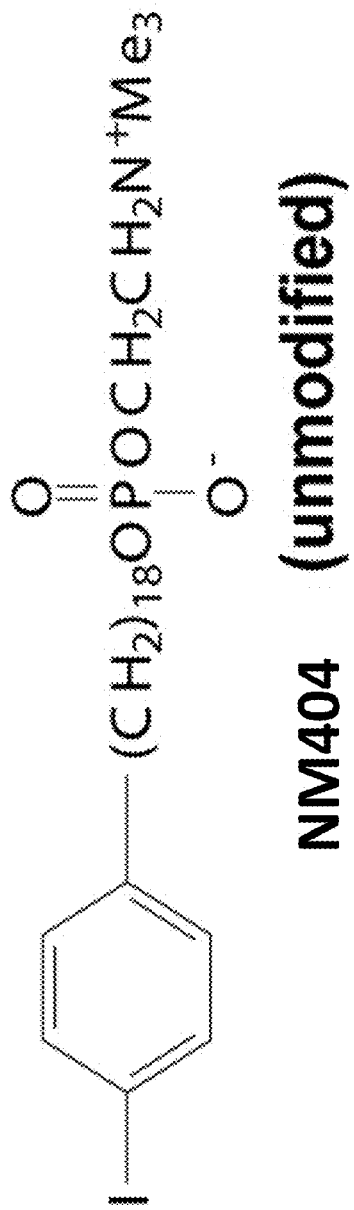
FIG. 1 shows the chemical structure of the base compound 18-(p-iodophenyl)octadecyl phosphocholine (NM404).

It is understood that this disclosure is not limited to the particular methodology, protocols, materials, and reagents described, as these may vary. The terminology used herein is for the purpose of describing particular embodiments only, and is not intended to limit the scope of the present invention, which will be limited only by any later-filed nonprovisional applications.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising" and variations thereof do not have a limiting meaning where these terms appear in the description and claims. Accordingly, the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art.

The terminology as set forth herein is for description of the embodiments only and should not be construed as limiting of the invention as a whole. Unless otherwise specified, "a," "an," "the," and "at least one" are used interchangeably and mean one or more than one.

The disclosure is inclusive of the compounds described herein (including intermediates) in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

"Pharmaceutically acceptable" as used herein means that the compound or composition or carrier is suitable for administration to a subject to achieve the treatments described herein, without unduly deleterious side effects in light of the necessity of the treatment.

The term "effective amount," as used herein, refers to the amount of the compounds or dosages that will elicit the biological or medical response of a subject, tissue or cell that is being sought by the researcher, veterinarian, medical doctor or other clinician.

As used herein, "pharmaceutically-acceptable carrier" includes any and all dry powder, solvents, dispersion media, coatings, antibacterial and antifungal agents, isotonic agents, absorption delaying agents, and the like. Pharmaceutically-acceptable carriers are materials, useful for the purpose of administering the compounds in the method of the present invention, which are preferably non-toxic, and may be solid, liquid, or gaseous materials, which are otherwise inert and pharmaceutically acceptable, and are compatible with the compounds of the present invention. Examples of such carriers include, without limitation, various lactose, mannitol, oils such as corn oil, buffers such as PBS, saline, polyethylene glycol, glycerin, polypropylene glycol, dimethylsulfoxide, an amide such as dimethylacetamide, a protein such as albumin, and a detergent such as Tween 80, mono- and oligopolysaccharides such as glucose, lactose, cyclodextrins and starch.

The term "administering" or "administration," as used herein, refers to providing the compound or pharmaceutical composition of the invention to a subject suffering from or at risk of the diseases or conditions to be treated or prevented.

A route of administration in pharmacology is the path by which a drug is taken into the body. Routes of administration may be generally classified by the location at which the substance is applied. Common examples may include oral and intravenous administration. Routes can also be classified based on where the target of action is. Action may be topical (local), enteral (system-wide effect, but delivered through the gastrointestinal tract), or parenteral (systemic action, but delivered by routes other than the GI tract), via lung by inhalation. One form of local administration referred to in this submission is intratumoral (IT), whereby an agent is injected directly into, or adjacent to, a known tumor site.

A topical administration emphasizes local effect, and substance is applied directly where its action is desired. Sometimes, however, the term topical may be defined as applied to a localized area of the body or to the surface of a body part, without necessarily involving target effect of the substance, making the classification rather a variant of the classification based on application location. In an enteral administration, the desired effect is systemic (non-local), substance is given via the digestive tract. In a parenteral administration, the desired effect is systemic, and substance is given by routes other than the digestive tract.

Non-limiting examples for topical administrations may include epicutaneous (application onto the skin), e.g., allergy testing or typical local anesthesia, inhalational, e.g. asthma medications, enema, e.g., contrast media for imaging of the bowel, eye drops (onto the conjunctiva), e.g., antibiotics for conjunctivitis, ear drops, such as antibiotics and corticosteroids for otitis externa, and those through mucous membranes in the body.

Enteral administration may be administration that involves any part of the gastrointestinal tract and has systemic effects. The examples may include those by mouth (orally), many drugs as tablets, capsules, or drops, those by gastric feeding tube, duodenal feeding tube, or gastrostomy, many drugs and enteral nutrition, and those rectally, various drugs in suppository.

Examples of parenteral administrations may include intravenous (into a vein), e.g. many drugs, total parenteral nutrition intra-arterial (into an artery), e.g., vasodilator drugs in the treatment of vasospasm and thrombolytic drugs for treatment of embolism, intraosseous infusion (into the bone marrow), intra-muscular, intracerebral (into the brain parenchyma), intracerebroventricular (into cerebral ventricular system), intrathecal (an injection into the spinal canal), and subcutaneous (under the skin). Among them, intraosseous infusion is, in effect, an indirect intravenous access because the bone marrow drains directly into the venous system. Intraosseous infusion may be occasionally used for drugs and fluids in emergency medicine and pediatrics when intravenous access is difficult.

The following abbreviations are used in this disclosure: ADCC, Antibody dependent cell-mediated cytotoxicity; B16, A melanoma syngeneic to C57Bl/6 mice; B78, A variant of B16 that expresses GD2, due to transfection with GD2 synthase; D, day; Hu14.18-IL2, The primary immunocytokine (reacts against GD2) used in the studies disclosed in the examples; IC, Immunocytoline (a fusion protein of a tumor-reactive mAb linked to IL2); IL2, Interleukin 2; IT, Intratumoral; IV, Intravenous; mAb, Monoclonal antibody; MAHA, Mouse anti-human antibody; NM404, used to designate the phospholipid ether shown in FIG. 1, which is selectively taken up by most tumors and used for TRT in the studies disclosed in the examples; NXS2, A neuroblastoma syngeneic to AJ mice; Panc02-GD2, A pancreatic cancer syngeneic to C57Bl/6 mice, expressing GD2, due to transfection with GD2 synthase; PLE, Phospho-lipid Ether; RT, Radiation therapy; TRT, Targeted radiotherapy; W, week; 9464D-GD2, A neuroblastoma syngeneic to C57Bl/6 mice, expressing GD2, due to transfection with GD2 synthase.

II. The Invention

This disclosure is directed to methods of treating any cancer that presents as one or malignant solid tumors. The disclosed methods combine two treatment steps, with an unexpected synergy resulting in a much improved in situ vaccination effect against the malignant solid tumors. Specifically, an immunomodulatory dose of a radiohalogenated compound that is differentially taken up by and retained within malignant solid tumor tissue is administered to the patient, and in situ tumor vaccination is performed by intratumorally injecting into (or applying to) at least one of the malignant solid tumors a composition that includes one or more agents capable of stimulating specific immune cells within the tumor microenvironment, either with or without additional xRT to at least one of the malignant solid tumors being treated with immune-stimulating agents. The immunomodulatory dose of the radiohalogenated compound likely reduces Treg levels (and other immune-suppressive elements) and prevents the immune system dampening (concomitant immune tolerance) that occurs when xRT is used against a tumor and one or more additional tumors are not radiated.

A. Intratumoral Immunization—In Situ Vaccination

Compositions used for intratumoral immunization may include, without limitation, one or more cytokines, immune checkpoint inhibitors, pattern recognition agaonists, and/or immunostimulatory monoclonal antibodies, including antibodies against tumor-specific antigens. For a review of intratumoral immunization/in situ vaccination strategies that are among those that could be used, see Pierce et al, Human Vaccines & Immunotherapoeutics 11(8):1901-1909, 2015; and Marabelle et al, Clin. Cancer Res. 20(7):1747-56, 2014; and Morris et al, Cancer Res., e-pub ahead of print, 2016; all of which are incorporated by reference herein. In the non-limiting examples disclosed herein, imtratumoral immunization was performed by injecting a fusion protein of an anti-GD2 mAb and interleukin 2 (hu14.18-IL2). However, the disclosed methods are not in any way limited by these examples.

B. Immunomodulatory Dose of a Radiohalogenated Compound

The radiohalogenated compound used must selectively target a wide range of solid tumor cell types, such that the RT emitted by the radiohalogenated compound is directed to malignant solid tumor tissue without substantially exposing other tissue types to the emitted RT. Radiohalogenated compounds having such characteristics include MIBG or the phospholipid ether analogs disclosed herein. The radioactive halogenated isotope included in the radiohalogenated compound may be any radioactive halogen isotope known to emit ionizing RT in a form that would result in immunostimulation of the cells that take up the compounds. In one non-limiting example, the incorporated radioactive halogen isotope is a radioactive iodine isotope, such as iodine-131.

The immunomodulatory RT dose (as opposed to injected dose) of the radiohalogenated compound is much less than the dose that would be used for conventional RT therapy against malignant solid tumors. Specifically, the dose must be sufficient to stimulate a response in immune cells within the tumor microenvironment (likely by reducing immune-suppressing Treg levels and other immunosuppressive cells or molecules), while not ablating the desired immune cells that are responsible for the in situ vaccine effect.

As noted in the examples, the proper immunomodulatory dose can be calculated from imaging data obtained after administering a "detection-facilitating" dose of a radiohalogenated compound. The detection-facilitating dose may be quite different than the immunomodulatory dose, and the radioactive halogen isotope that is incorporated into the radiohalogenated compound may be different (although the rest of the compound structure should be the same). The radioactive halogen isotope used in the detection step and dosimetry calculations may be any radioactive halogen isotope known to emit RT in a form that is readily detectable by conventional imaging means. Non-limiting examples of "conventional imaging means" include gamma ray detection, PET scanning, and SPECT scanning. Non-limiting examples of radioactive halogen isotopes that could be used include astatine-211, iodine-123, iodine-124, iodine-125, and iodine-131.

C. Methods of Synthesizing the Disclosed Analogs and Compositions

The alkylphosphocholine analogs used in the disclosed methods are known in the art, as are methods of synthesizing such analogs. For details regarding synthetic materials and methods, see, e.g., U.S. Patent Publication Nos. 2010/0284929, 2010/0316567, 2012/0128596, 2014/0030187, and 2014/0023587, each of which is incorporated by reference herein in its entirety. Similarly, methods and compositions used in in situ vaccination/intratumoral immunization cancer therapies are known in the art.

D. Application to a Wide Range of Adult and Pediatric Solid Tumors

As noted above, we have previously demonstrated that the alkylphosphocholine analogs used in the disclosed methods are selectively taken up in a wide range of adult and pediatric solid tumors, as confirmed by both in vivo imaging and tumor growth inhibition studies.

It is well-known in the art that the relative radiosensitivity of solid tumor cancer cell phenotypes ranges from those that have very low RT sensitivities (e.g., pancreas, colorectal, glioma and breast) to those with high RT sensitivities (e.g., lymphomas). A tumor with low radiosensitivity is considered to be highly radioresistant and a highly radiosensitive tumor is considered to have low radioresistance. Relative radiosensitivity of cancer cells is commonly presented as the fraction that survives 2-Gy of in vitro RT exposure ($SF_2$). Cancers can be categorized or ranked by their relative radiosensitivity, and Table 1 provides non-limiting examples of known $SF_2$ values for some common solid tumors.

TABLE 1

Relative Radiosensitivity of Select Cancer Cell Types

| Tumor Type | Cell Line | $SF_2$ value |
|---|---|---|
| Breast | MDA-MB-231 | 0.82 |
| Pancreatic | Mia-Paca | 0.80 |
| Colorectal | HCT-29 | 0.75 |
| Melanoma | B-78 | 0.65 |
| Glioma (brain) | U-87 | 0.63 |
| Lung (NSCLC) | A-549 | 0.61 |
| Prostate | PC-3 | 0.55 |
| Lymphoma | EL-4 | 0.30 |

$SF_2$ = surviving fraction following exposure to 2 Gy of in vitro RT exposure
* Several cell lines We have previously demonstrated good tumor uptake and growth inhibition with the disclosed compounds in a wide range of tumor types, including both highly radiosensitive tumors like lymphoma and also in highly RT resistant tumors like glioma, breast, pancreatic or colorectal tumors. Thus, quantitative imaging and dosimetry can be used without undue experimentation to quantify the RT dose necessary to stimulate the immune system in a wide variety of solid tumor types.

E. Dosage Forms and Administration Methods

In situ vaccination can be performed by intratumoral injection, but other administration can apply (topical or systemic). For the synergistic targeted RT, any route of administration may be suitable. In one embodiment, the disclosed alkylphosphocholine analogs may be administered to the subject via intravenous injection. In another embodiment, the disclosed alkylphosphocholine analogs may be administered to the subject via any other suitable systemic deliveries, such as parenteral, intranasal, sublingual, rectal, or transdermal administrations.

In another embodiment, the disclosed alkylphosphocholine analogs may be administered to the subject via nasal systems or mouth through, e.g., inhalation.

In another embodiment, the disclosed alkylphosphocholine analogs may be administered to the subject via intraperitoneal injection or IP injection.

In certain embodiments, the disclosed alkylphosphocholine analogs may be provided as pharmaceutically acceptable salts. Other salts may, however, be useful in the preparation of the alkylphosphocholine analogs or of their pharmaceutically acceptable salts. Suitable pharmaceutically acceptable salts include, without limitation, acid addition salts which may, for example, be formed by mixing a solution of the alkylphosphocholine analog with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

Where the disclosed alkylphosphocholine analogs have at least one asymmetric center, they may accordingly exist as enantiomers. Where the disclosed alkylphosphocholine analogs possess two or more asymmetric centers, they may additionally exist as diastereoisomers. It is to be understood that all such isomers and mixtures thereof in any proportion are encompassed within the scope of the present disclosure.

The disclosure also includes methods of using pharmaceutical compositions comprising one or more of the disclosed alkylphosphocholine analogs in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for parenteral, intranasal, sublingual or rectal administration, or for administration by inhalation or insufflation.

For preparing solid compositions such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid pre-formulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the alkylphosphocholine analogs may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium caboxymethylcellulose, methylcellulose, polyvinylpyrrolidone or gelatin.

The disclosed alkylphosphocholine analogs are particularly useful when formulated in the form of a pharmaceutical injectable dosage, including in combination with an injectable carrier system. As used herein, injectable and infusion dosage forms (i.e., parenteral dosage forms) include, but are not limited to, liposomal injectables or a lipid bilayer vesicle having phospholipids that encapsulate an active drug substance. Injection includes a sterile preparation intended for parenteral use.

Five distinct classes of injections exist as defined by the USP: emulsions, lipids, powders, solutions and suspensions. Emulsion injection includes an emulsion comprising a sterile, pyrogen-free preparation intended to be administered parenterally. Lipid complex and powder for solution injection are sterile preparations intended for reconstitution to form a solution for parenteral use. Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization. Solution injection involves a liquid preparation containing one or more drug substances dissolved in a suitable solvent or mixture of mutually miscible solvents that is suitable for injection.

Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Introduction to the Examples

These examples demonstrate the potential of bringing together two very distinct cutting-edge disciplines in cancer treatment research, capitalizing on an unexpected and very potent synergy. These disciplines are: 1) systemically administered TRT and 2) locally-directed, antibody-mediated, cancer immunotherapy. The data presented herein suggest that powerful synergy results from combining these approaches. Together, these two strategies can be used to destroy visible macroscopic tumor in a way that enables the destroyed cancer cells to function as a potent in situ vaccine that creates tumor-specific T cell immunity able to eradicate persistent residual metastatic disease, for any type of solid tumor in any location.

Our ongoing preclinical work has shown that combination of tumor-specific mAb with IL2 (to activate innate immune cells) results in augmented antibody-dependent cell-mediated cytotoxicity (ADCC) [1,2]; a process that has already been translated into clinical benefit for children with neuroblastoma [3]. Recent preclinical data demonstrate more potent antitumor efficacy when the mAb-IL2 fusion protein is injected intratumorally (IT) [4,5]. Remarkably, large tumors that do not respond to these mAb/IL2 injections and continue growing if treated only with local xRT, can be completely eradicated if the xRT is combined with the mAb/IL2 treatment. Most mice are cured and develop T cell memory that rejects re-challenge with similar tumor cells [6]; demonstrating that the combined xRT+mAb/IL2 is acting as a potent "in situ" anti-cancer vaccine.

A key limitation is that if there is another macroscopic tumor present in these animals when they receive xRT+mAb/IL2 treatment to the primary (first) tumor, the second tumor will continue to grow and, to our surprise, suppress the immune response, preventing any shrinkage of the $1^{st}$ treated tumor. This "concomitant immune tolerance" results, in part, from suppressive regulatory T cells (Tregs) in the $2^{nd}$ tumor. Delivering RT alone to both tumors has minimal anti-tumor effect, but does deplete these Tregs. Thus, when first tumors are treated with xRT+mAb/IL2, the addition of RT to the second tumor circumvents this immune tolerance, enabling eradication of both tumors [7]. These observations indicate a limitation of in situ tumor vaccination in the metastatic setting, but also suggest a robust capacity of RT to overcome this limitation.

xRT cannot typically be delivered to all metastatic sites without prohibitive normal tissue toxicity and immune suppression. Yet not delivering xRT to all sites of macroscopic disease may leave inhibitory immune lineages intact, which are capable of suppressing the immunologic response to our local xRT+mAb/IL2 immunotherapy. What is needed, therefore, is a means to deliver RT to all tumor sites in a cancer patient in a targeted manner.

We have developed TRT vehicles capable of targeting systemically administered RT to both primary and metastatic cancers. One such TRT agent, $^{131}$I-NM404, An intravenously (IV) administered phospholipid ether (PLE) analog, has shown nearly universal tumor targeting properties in over 60 in vivo cancer and cancer stem cell models. This agent is currently being evaluated clinically in multiple imaging and therapy trials [8,9]. A systemic injection of $^{131}$I-NM404 localizes in all tumors regardless of anatomic location and internally provide sufficient RT to ablate intratumoral immunosuppressive pathways that can prevent development of an effective, tumor-eradicating, immune response. The unique attributes of this approach are the near universal tumor targeting capability of NM404, as well as the ability to deliver immunomodulatory sub-lethal doses of RT to all tumor sites, something that is not typically feasible with xRT. What is new about this is that our TRT Agents may immuno-modulate all tumors regardless of anatomic location, overcoming concomitant tolerance, which will result in a long-term in situ tumor vaccination effect following local xRT followed by injection of a tumor specific mAb+IL2. As an increasing number of tumor specific mAbs are becoming approved for clinical use, this combination strategy could be readily expanded to clinical application for any tumor type that can be targeted by a tumor-reactive mAb. Furthermore, the approach can be readily generalized to all in situ tumor vaccination strategies.

In these examples, we describe how to assess the ability of $^{131}$I-NM404 and related analogs to initiate the systemic immunomodulatory response necessary to enable local combined xRT+mAb/IL2 treatment to induce a potent radioimmune-facilitated in situ cancer vaccine. A similar assessment could be done for combined PLE analog-delivered TRT with other in situ cancer vaccine methods.

In sum, we disclose herein the first effort to combine two different methods from seemingly disconnected cancer therapy disciplines into a single unified treatment. The data presented in these examples indicate that the two methods can be synergistically combined to effectively eliminate malignant solid tumors and to prevent tumor recurrence. The three key concepts underlying this approach are that (A) local xRT+IT mAb/IL2 eradicates an existing single tumor and generates T-cell memory (an in situ vaccine); (B) unless irradiated, distant tumors cause concomitant immune tolerance, preventing in situ vaccine efficacy; and (C) unlike whole body RT, TRT can localize to all tumors, without severe systemic RT-induced immune suppression. These concepts, together with our data, lead to the conclusion that xRT+IT mAb/IL2 to a mouse's primary tumor, plus TRT to eliminate tolerance caused by metastases, will enable effective in situ vaccination to eradicate all malignant solid tumor-based cancers (primary and metastatic sites).

In Example 1, we present background data from our B78 GD2+ model in support of the claimed method.

In Example 2, we provide guidance for determining the dose of xRT needed for optimal in situ vaccine effect to a primary tumor, and the lowest dose of xRT to a distant tumor needed to prevent concomitant immune tolerance.

In Example 3, we provide guidance for determining the $^{131}$I-NM404 dosing that approximates the required dosing of xRT to metastases, as determined in Example 2, and subsequently evaluating the effects of that $^{131}$I-NM404 dose on in vivo immune function.

In Example 4, we provide guidance for using data from Examples 2 and 3 to design/test/develop a regimen of $^{131}$I-NM404+local xRT+IT-mAb/IL2 in mice bearing two or more tumors in order to destroy the locally treated tumors and induce T-cell mediated eradication of all distant tumors. Critical issues of TRT and xRT dose and time are optimized for antitumor efficacy.

In Examples 5, 6, 7 and 8, we provide information and specific data from experimental studies performed in accordance with the guidance of Examples 1-4.

Example 1: Background Supporting Data

The Sondel lab has shown that tumor-specific mAb+IL2 activates innate immune cells to mediate ADCC in mice [2], with clinical benefit for children with neuroblastoma [3]. In mice, IV administration of the hu14.18-IL2 IC is more potent than IV administration of anti-GD2 mAb+IL2 [2, 10]. This can provide dramatic antitumor effects against very small recently established GD2+ tumors or very small microscopic metastases, potentially accounting for the clinical use of this approach in patients in remission but at great risk for relapse [3]. More potent antitumor efficacy against measurable, macroscopic tumors [i.e. ~50 mm$^3$ GD2+ tumors] can be achieved when the IC is injected intratumorally (IT-IC) rather than IV [4,5].

Figure 2A:
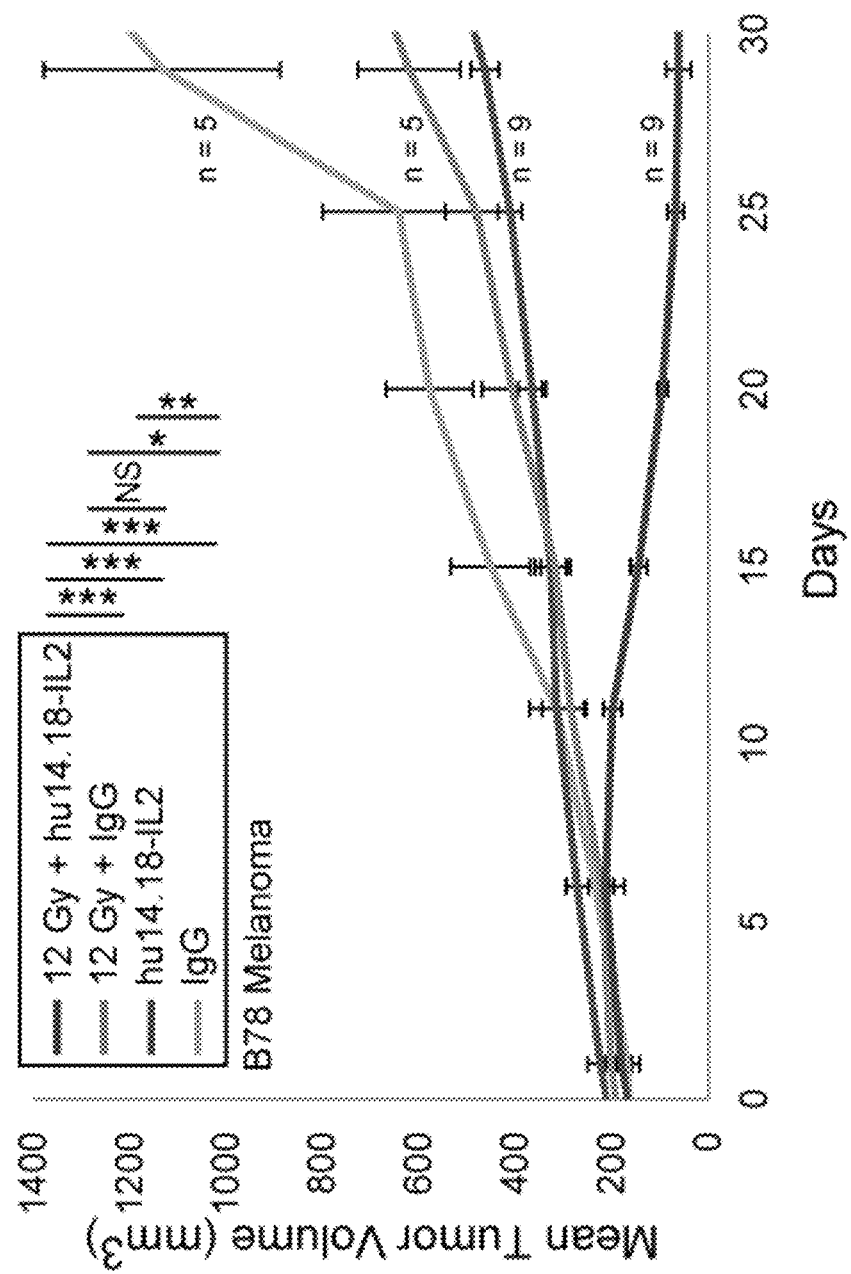
FIGS. 2A, 2B and 2C are a series of graphs showing that xRT+IT-IC elicits in situ tumor vaccination. 2A) Tumor growth curves and 2B) Kaplan-Meier survival curves show synergy between xRT and IT-hu14.18-IL2. 71% (22/31) of mice treated with xRT+IT-IC are rendered disease-free. 2C) 90% of these reject subsequent engraftment with B78 melanoma.
Figure 2B:
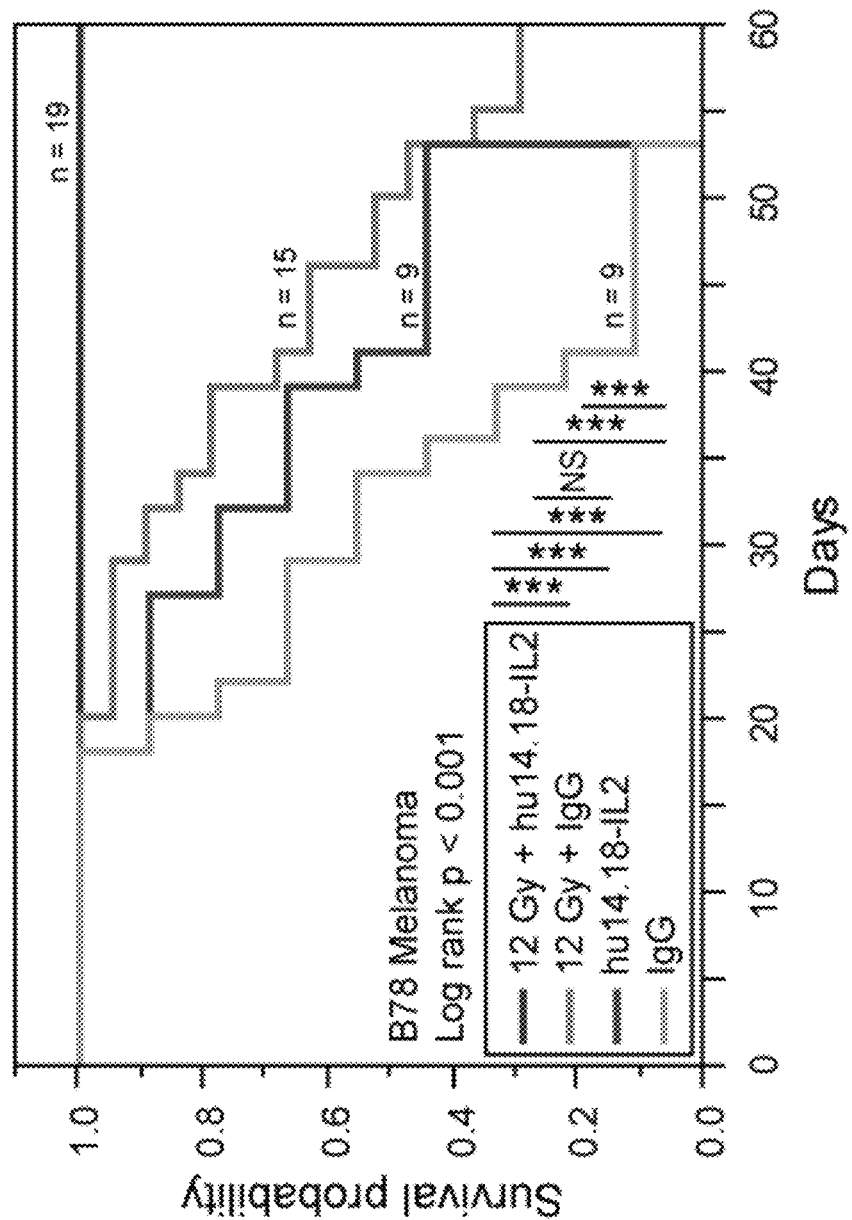
Figure 2C:
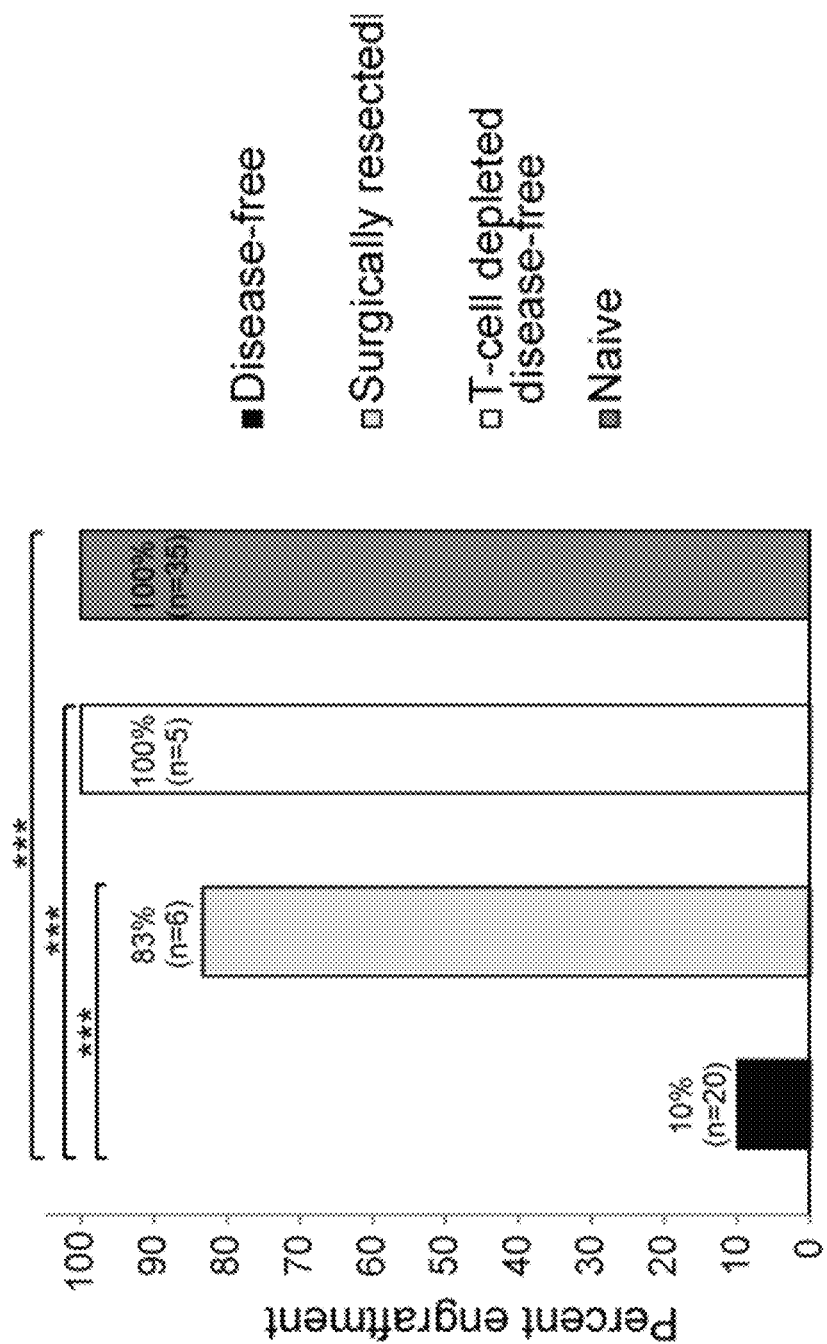

We are now focusing on ways to provide benefit in the setting of much larger, macroscopic tumors. Mice bearing a moderately large (200 mm$^3$) B78 melanoma tumor, established five weeks earlier, show no response to IV-IC, and are slowed in their growth by IT-IC, but the tumors continue to grow. These same 200 mm$^3$ tumors also grow after 12 Gy of xRT. In contrast, when the IT-IC and xRT are combined, 73% of the animals become tumor-free and appear cured of their disease (FIGS. 2A and 2B). These mice then show T-cell mediated rejection of rechallenge with the same tumor (FIG. 2C). Thus IT-IC+xRT synergize, inducing the tumor to become an "in situ tumor vaccine" [6].

Figure 3:
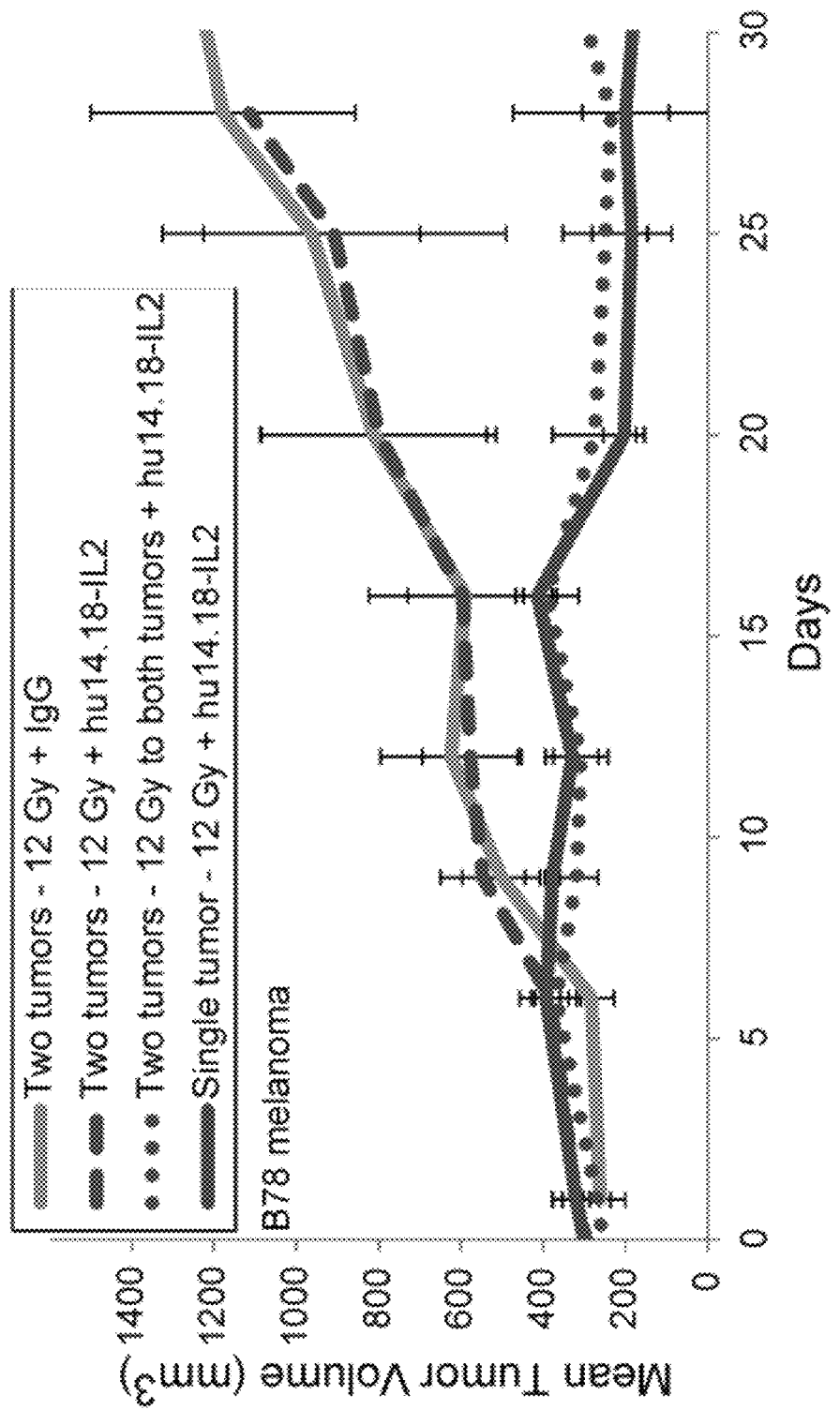
FIG. 3 is a graph demonstrating concomitant immune tolerance. Primary tumor response is shown. A distant un-treated tumor suppresses response to xRT+IT-IC in a 2-tumor B78 melanoma model, and this suppression can be overcome be radiating the second tumor.
Figure 4:
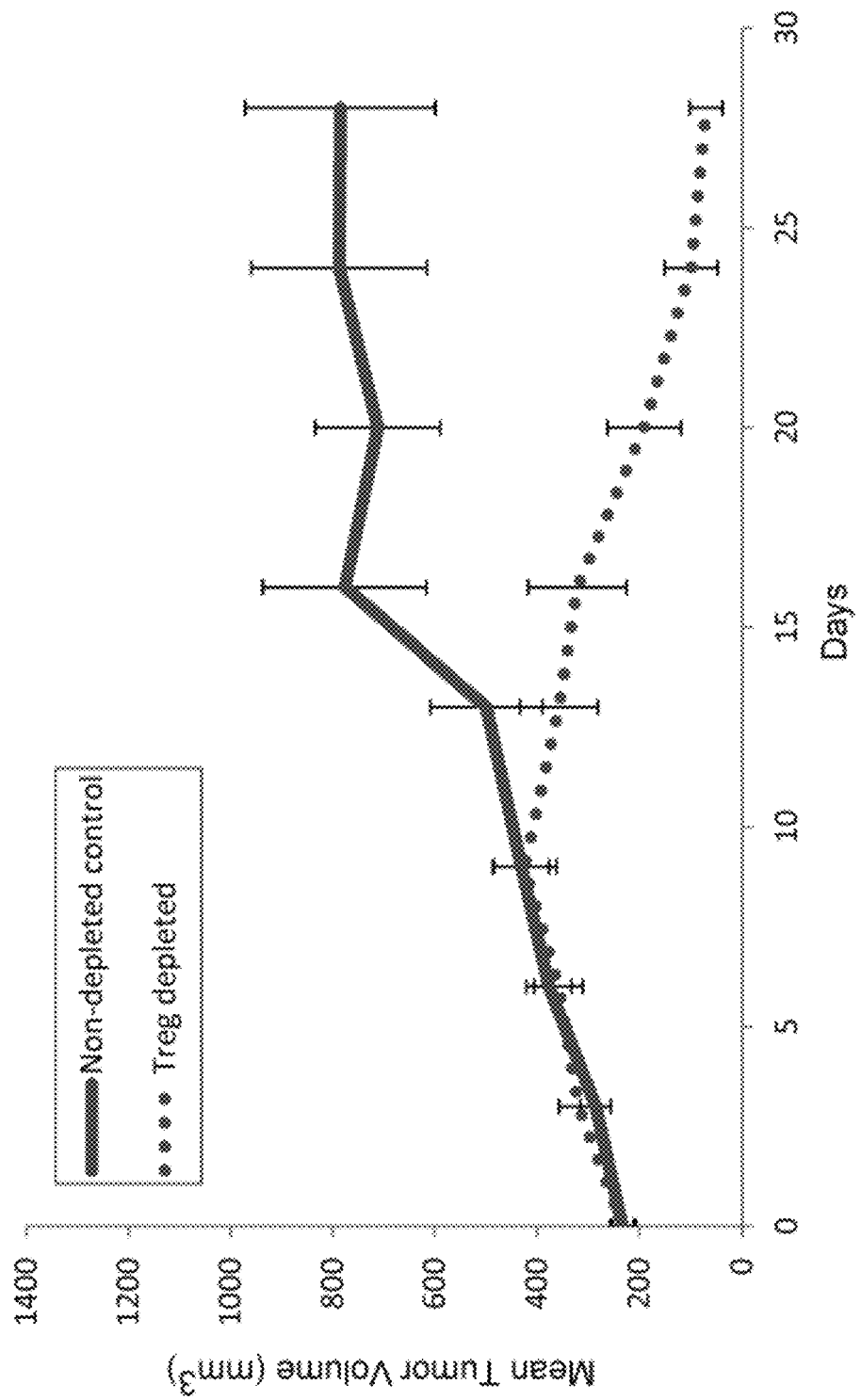
FIG. 4 is a graph showing that concomitant immune tolerance is due to Tregs. Primary tumor response is shown. A distant un-treated tumor suppresses response to xRT+IT-IC in a 2-tumor B78 melanoma model and this suppression can be overcome by depleting Tregs (using transgenic DEREG mice that express diphtheria toxin receptors on their Tregs, and thus depleting Tregs by administering diphtheria toxin).

In order to simulate clinical metastases, we inoculate mice with B78 in one flank on d-1, and the other flank at week 2. At week 5, the first tumor is 200 mm$^3$, and the second is 50 mm$^3$. We anticipated that xRT+IT-IC would destroy the first tumor and that the resultant T cell response would then destroy the second. However, adding IT-IC to the xRT had virtually no effect on either the 50 mm$^3$ tumor or the 200 mm$^3$ tumor (FIG. 3). This demonstrated a key limitation to the therapy we delivered; namely, if there is another tumor present when these moce receive xRT+IT-IC to the first tumor, the second tumor will cause a systemic tumor-specific concomitant immune tolerance effect, preventing any shrinkage of either tumor. Importantly, we have found that local xRT (12 Gy) to the first and second tumor simultaneously, abrogates this tolerance effect, allowing IT-IC to the first tumor to induce an immune response that eradicates both tumors in most mice (FIG. 4) [7]. Recent data, using a Treg depleting mAb (not shown) or transgenic mice that allow selective Treg depletion (FIG. 4) [7], demonstrate that this immune tolerance is mediated, in part, by regulatory T cells (Tregs); RT to the first and second tumors partially deplete these Tregs, potentially explaining how irradiating both tumors circumvents the tolerance effect [7].

While local xRT to both the first and second tumors circumvents tolerance, clinical metastatic disease is often in several locations. All macroscopic metastatic disease must receive RT to block immune tolerance and enable xRT+IT-IC to effectively eradicate all tumor sites. However, delivery of 12 Gy xRT to all sites of disease may be akin to "total body RT" with major dose-dependent (potentially lethal) toxicity and profound systemic immune suppression.

Previously, the Weichert lab has pioneered the development of TRT, in order to deliver RT to all systemic tumor sites, while minimizing "off-target" RT to normal tissue (especially marrow and immune tissue).

Figure 5:
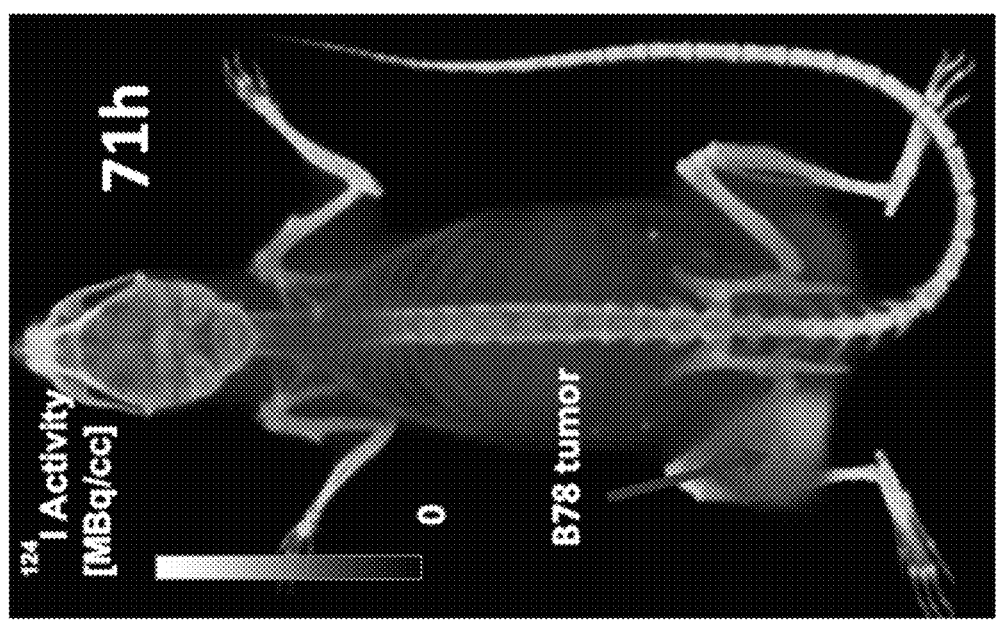
FIG. 5 is an image showing selective uptake of $^{124}$I-NM404 by B78 melanoma. A mouse bearing a ~200 mm$^3$ B78 tumor received IV $^{124}$INM404 and had serial PET/CT scans done. This image at 71 h shows selective uptake by the tumor with some residual background uptake by the heart and liver.

Based on the finding that tumor cells contain an overabundance of phospholipid ethers (PLE) [11], we synthesized over thirty radioiodinated PLE analogs in hopes of identifying analogs that would selectively target tumors [12]. One of these, NM404, not only displayed near universal tumor uptake in all but three of over 70 in vivo models examined regardless of anatomic location, including brain metastases and cancer stem cells, but also underwent prolonged selective retention once it entered tumor cells [8]. These diapeutic PLE analogs are unique in that they avoid premalignant and inflammatory lesions. Surface membrane lipid rafts, which are overexpressed on cancer cells relative to normal cells, serve as portals of entry for PLE's, including NM404, into cancer and cancer stem cells [8]. Radioiodinated NM404 (I-124 and I-131), which has now been evaluated in five phase 1 and 2 PET imaging trials and three phase 1 TRT radiotherapy trials, respectively, affords similar tumor uptake and retention properties in over a dozen human cancer types [8]. Excellent tumor uptake in the cancer models relevant to these examples (the B78 GD2+ murine melanoma) have been confirmed with $^{124}$-NM404 PET imaging (FIG. 5).

Example 2: Determining Dosages of xRT

Our data suggest these four hypotheses: (1) the dose of xRT we have used to treat a single tumor causes modest direct in vivo tumor death and increases susceptibility to immune mediated death (via both ADCC and T cells); (2) the strong T-cell response provided by the addition of IT-IC, but not IT mAb, suggests that mAb binding to radiated tumor cells, in the presence of IL2, facilitates antigen presentation and augmented induction of adaptive immunity; (3) the presence of a second tumor prevents the xRT+IT-IC to the first tumor from causing virtually any anti-tumor effect, due to tolerance caused largely by the systemic actions of immunosuppressive cells present in the second tumor [such as Tregs and possibly myeloid derived suppressor cells (MDSC)]; this tolerance can be circumvented by depletion of Tregs (FIG. 4) or irradiating the second tumor (FIG. 3); (4) the dose of RT needed at the second tumor to circumvent tolerance might be much lower than the xRT dose needed for the first tumor to become an "in situ vaccine" [14].

Optimizing xRT Dose for the Primary ("In Situ Vaccine") Tumor Site.

Our in vivo studies of xRT+IT-IC have focused on one dose of 12 Gy to the first tumor. This is based on our data showing that in vitro RT induces a dose-dependent functional upregulation of Fas on B78 tumor cells (nearing peak at >12 Gy), coupled to our in vivo data demonstrating our in situ vaccine effect of xRT+IT-IC requires mice with functional Fas-L (6). We conducted in vivo pilot studies prior to selecting the 12 Gy dose, which showed higher dose (16 Gy) or increased fractionation flank RT had toxicity (dermatitis, ulceration, and late limb edema) and no improvement in tumor response. While we chose a 12 Gy single fraction of xRT for our in vivo studies, as we move towards clinical translation, it will be beneficial to better understand the mechanism of the local xRT effect and its dose requirements, in order to safely and effectively induce the in situ vaccine effect.

Our mouse data (FIGS. 2A, 2B and 2C) show that we can induce a potent vaccine effect with 12 Gy xRT+IT-IC, even though 12 Gy of xRT alone causes no shrinkage of the tumor; it merely slows the progressive growth. We might see just as potent an in situ vaccine effect using lower doses of RT. To test this, we will evaluate a range of xRT doses (from 4-16 Gy) as a single fraction in mice bearing a ~200 mm$^3$ B78 tumor, followed by our standard IT-IC regimen (50 mcg/d on days 6-10). We will determine which xRT doses give optimal tumor eradication and T-cell memory, when combined with IT-IC. If doses lower than 12 Gy are less toxic and show comparable efficacy, such lower doses would be better targets for our xRT dose to the "in situ vaccine" site in Examples 3 and 4.

Optimizing xRT Dose at a Distant Tumor to Prevent Tolerance from Blocking "In Situ Vaccination."

Treating both the first and second tumors with 12 Gy (FIG. 3) enables IT-IC to the first tumor to induce a potent response that eradicates both tumors. Our goal is to be able to accomplish this same in situ vaccine effect by providing xRT+IT-IC to a single tumor while using the minimal RT dose necessary at metastatic sites to circumvent tolerance. We recognize that xRT itself, especially if widespread, can be myelo/immunosuppressive. This is why we are pursuing TRT in Examples 3 and 4. Even though it is targeted, TRT does have some systemic delivery of RT. In order to minimize the systemic immune suppression from TRT, we wish to give as low of a dose of TRT as is needed to effectively inhibit the tumor-induced immune tolerance, while not causing systemic RT-induced global immune suppression. Therefore, we will determine how low of a dose of xRT needs to be delivered to the distant tumor in order to enable a higher xRT dose to the first tumor to function as an in situ vaccine when combined with IT-IC to the first tumor.

Mice bearing a 200 mm³ first B78 tumot and a ~50 mm³ second B78 tumor will receive 12 Gy of xRT to the first tumor on day-0 (~5 weeks after implantation of the first B78 tumor). This will be followed by our standard regimen of IT-IC on days 6-10. Separate groups of mice will receive varying doses of xRT to the second tumor. Based on data from the lab of B. Johnson demonstrating that a total body xRT of 3 Gy can prevent an immunosuppressive effect in a myeloma model (15), we will evaluate doses of 0, 1, 5 and 8 Gy (in addition to the 12 Gy dose we know is effective). We will see if doses substantially less than 12 Gy to the second tumor can be as effective as the full 12 Gy dose at eliminating the immune tolerance.

Once we have clarified the critical dose of xRT where we lose the beneficial effect, we will perform subsequent analyses to better identify the critical dose. For example, if 5 Gy is as effective as 12 Gy, but 1 Gy is not much better than 0 Gy, we would then compare 2, 3, and 4 Gy to identify the critical lowest effective RT dose needed to eliminate tolerance and obtain efficacy in this two tumor model, receiving 12 Gy+IT-IC to the first tumor.

Repeat studies would then be done to confirm if this lowest effective dose to the second tumor still enables an effective in situ vaccine when the dose to the first is the lowest effective dose in the 1-tumor model (tested in Example 2, above) rather than the 12 Gy dose. In summary, the studies of Example 2 will determine what the lowest xRT doses are for the first and second tumors, without losing the efficacy we have demonstrated with 12 Gy to both.

Initiating Studies of Required xRT Dose to First and Second Tumors in Mice Bearing Tumors Other than B78.

To allow our mouse studies to suggest more clinical generalizability, we will initiate analyses of RT+IT-IC in additional models of GD2+ tumors. We have published on IT-IC with hu14.18-IL2 IC in AJ mice bearing the GD2+ NXS2 neuroblastoma [5]. We are also evaluating IT-IC with this same IC in C57BL/6 mice bearing the GD2+ 9464D-GD2 neuroblastoma, and the Panc02-GD2 pancreatic cancer that express GD2 via our insertion of the gene for GD2 synthase. As for Example 2, for each model we will determine the lowest effective xRT dose needed to the primary and the secondary tumors to retain the in situ vaccine effect.

Example 3

Determining Dosage of $^{131}$I-NM404 and Evaluating Effects on Immune Function
Dosimetry with TRT and Immunesuppression from TRT in C57BL/6 Mice.

$^{131}$I-NM404 has shown selective uptake in vitro in >95% of tumor lines (human and mouse), with poor uptake by non-malignant cells, and with similar tumor specificity seen in vivo. This includes selective uptake in vivo with the B78 tumor (FIG. 5). In our preliminary dosimetry study, we gave $^{124}$I-NM404 to C57BL/6 mice and characterized the time course of TRT exposure by serial PET/CT imaging (as in FIG. 5). Monte Carlo dosimetry calculations [16-18] based on this study indicated that ~60 μCi of $^{131}$I-NM404 would be needed to deliver ~3 Gy to an established B78 tumor over a four week period of decay. After those four weeks, the remaining TRT dose to the B78 tumor would be less than 0.25 Gy. We will replicate the data we obtained in our 2-tumor model using xRT (FIG. 3), but use the lowest possible dose of targeted $^{131}$I-NM404 TRT to enable effective elimination of tumor-induced tolerance at all sites of distant disease. However, unlike xRT, which delivers all dose in minutes and is then done, TRT deposits dose over time, depending upon both the biological and physical half-life of the targeted isotope (8 day t½ for $^{131}$I). We want an initial TRT effect at the distant tumor sites to eradicate immune tolerance; however we want the immunosuppressive TRT effect to then be minimal when we give the IT-IC to induce ADCC and the in situ vaccine anti-tumor effects. This is essential to allow full tumor destruction at all sites.

Figure 6:
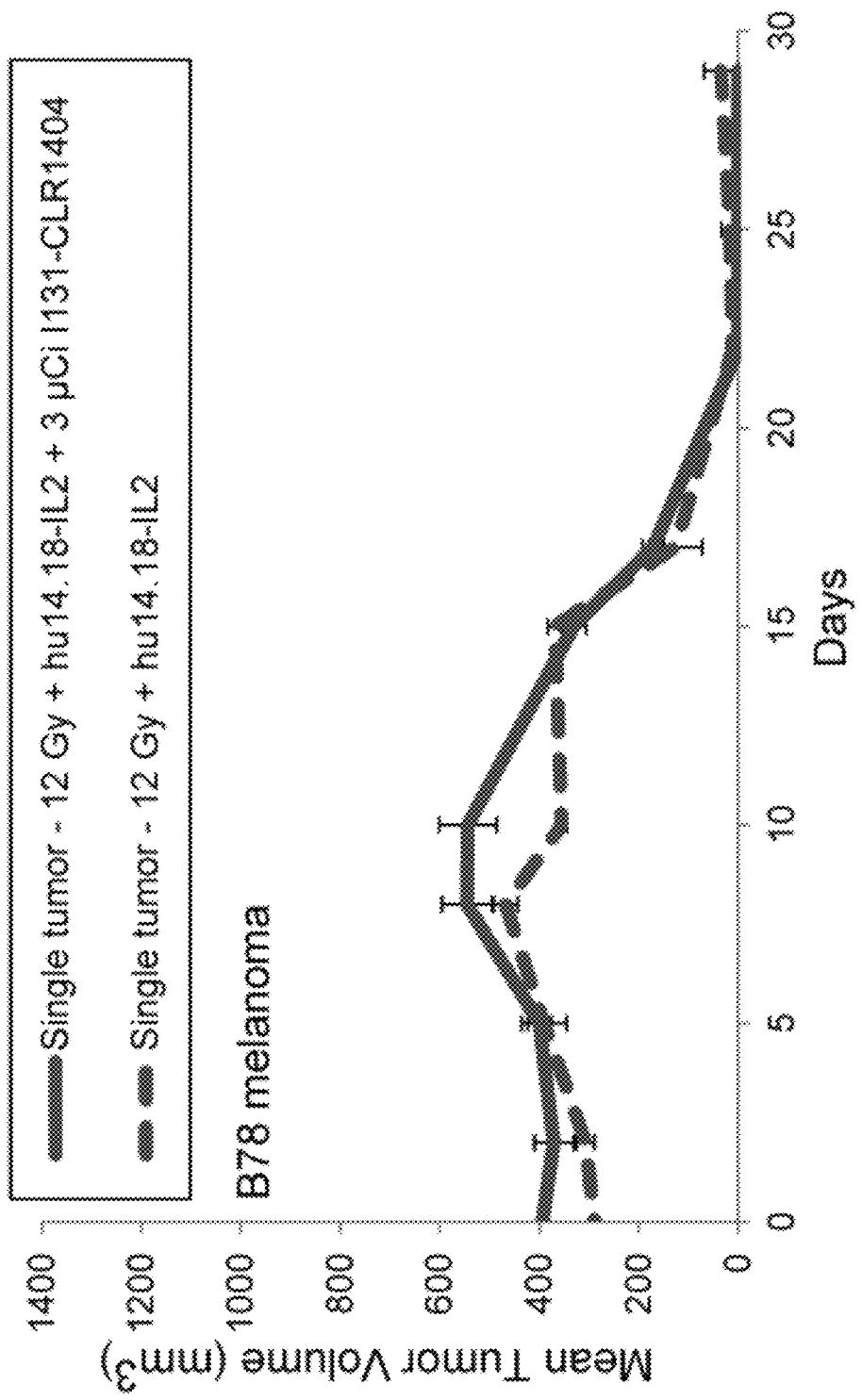
FIG. 6 is a graph demonstrating that in situ vaccination can be elicited in the presence of residual levels of molecular targeted radiation therapy (TRT). Treatment with combined xRT+IT-IC is equally effective in the presence or absence of 3 µCi 131I-NM404. This approximates the residual activity of TRT that will be present when we deliver xRT (d0) followed by IT-IC (d6-10), as described in Example 4.

Using the dosimetry calculations from our preliminary data, we estimated that a dose of 3 μCi of $^{131}$I-NM404, should deliver an equivalent of ~0.2 Gy to the tumor site, a dose that we hypothesized should not be immunosuppressive and should not prevent lymphocyte-mediated tumor destruction. As noted above, this is the dose we estimated would remain yet to be delivered 28 days after an initial $^{131}$I-NM404 dose of 60 μCi. We thus evaluated groups of mice bearing a single 200 mm³ B78 tumor. On day 0, all mice got 12 Gy xRT to their tumor, and on days 6-10, all got 50 mcg/d of IT-IC. One group also got 3 μCi of $^{131}$I-NM404 on d-0 (~0.2 Gy). FIG. 6 shows that the group receiving the $^{131}$I-NM404 had the same degree of tumor eradication as the group without $^{131}$I-NM404, demonstrating that this low dose of "residual" TRT in the tumor does not block immune mediated destruction by the RT+IT-IC in situ vaccine. We thus hypothesize that if we would use an initial dose of 60 μCi of $^{131}$I-NM404 TRT on day-22, it would effectively block the tolerogenic effect of distant tumors, yet enable xRT on day 0 and IT-IC on days 6-10 (28 d after the TRT) to the first tumor to function as an in situ vaccine, inducing an adaptive response that then eradicates all tumors.

The experiments outlined in this example will evaluate the dose relationships tested in FIG. 6. In our 1-tumor B78 model, we will test a range of doses of $^{131}$I-NM404 TRT to determine what TRT dose would result in enough unwanted systemic immune suppression to interfere with the desired in situ vaccine effect (and thereby slow or prevent eradication of the first tumor). This is important to Example 4, as it will allow us to make sure the residual radioactivity of the TRT has decayed to less than this value at the time we initiate IT-IC to the first tumor in mice with distant disease. We will also evaluate the kinetics of the TRT response after varying TRT doses to determine how long we must wait after the "tolerance-preventing TRT dose" is given to animals with multiple tumors to allow the RT+IT-IC treatment of the first tumor to still induce the in situ vaccine effect and eradicate the primary as well as distant tumors.

Related studies will also look at what dose of TRT, given as single agent treatment, would be required to cause slowing, versus shrinkage, versus eradication of a single B78 tumor. The dose of TRT that will be needed to eliminate the tumor-induced immune tolerance will be substantially less than the TRT dose needed to actually induce complete tumor destruction (from the TRT alone).

Finally, once the effects of various doses of TRT are determined in the 1-tumor model, we will evaluate the subtle immune-suppressive effects of TRT, by evaluating sera from these mice for their immune response to the human IgG component of the IC. We have shown that immunocompetent mice generate a readily quantified level of Mouse Anti-Human Antibody (MAHA) following treatment with these humanized ICs (19). We will use this as a means of determining at what dose we are seeing the TRT cause a detectable dose-dependent decrease in the strength of the murine immune response, to gauge the overall immunosuppressive effects from the systemic doses of RT these mice will receive from this TRT. The low TRT dose that we will need to block the tumor-induced immune tolerance will cause minimal systemic immune suppression.

Dosimetry with TRT and Immunesuppression from TRT in A/J Mice.

As in Example 2, once we are nearing completion of the studies outlined above, we will begin initiating selective replicate studies in A/J mice bearing the NXS2 neuroblastoma.

Example 4: Developing a Regimen of $^{131}$I-NM404+Local xRT+IT-mAb/IL2 in Mice Bearing Two or More Tumors Testing the Efficacy of TRT+xRT+IT-IC in the 2-Tumor B78 Model.

The dose and timing information learned from the studies outlined in Examples 2 and 3 will provide the information we need to estimate TRT dosing and timing required for efficacy in our 2-tumor model. C57BL/6 mice will be inoculated with B78 in the left (L) and right (R) flanks simultaneously. Each tumor should be ~50 mm$^3$ after two weeks and ~200 mm$^3$ after five weeks. If we assume that our dosimetry calculations in Example 3 suggest that we need to deliver 60 µCi of TRT to approximate 3 Gy RT to the second tumor (to block the immune tolerance), our xRT studies predict that this dose should have minimal slowing effect on tumor growth. We would plan to treat different groups of mice with 30, 60 or 90 µCi at the 2 w time point (when the tumors are ~50 mm$^3$). Three weeks later the tumors should be ~200 mm$^3$; at that time we will give xRT (dose determined as outlined in Example 2) followed six days later (~28 d after the TRT) by five daily injections of IT-IC to the tumor in the L flank, to induce the in situ vaccine effect. Control mice would get no TRT, and only the xRT and IT-IC to the L flank, anticipating no in situ vaccine due to tolerance from the distant tumor. A separate group would get local xRT to both tumors and IT-IC to the L flank, anticipating eradication of both tumors via the in situ vaccine effect. Another group would get TRT+IT-IC, but without local xRT, anticipating an incomplete vaccine effect.

Follow-up experiments would further evaluate varying doses of TRT and variations in the timing between the TRT and the local xRT+IT-IC to the primary tumor (L flank). The readouts will be: (A) eradication of the primary tumor; (B) eradication of the secondary tumor; and (C) systemic immune suppression, via ELISA analyses of the MAHA response. Our goal is to identify TRT dose and timing, to add to the local xRT+IT-IC regimen that can eradicate both tumors in most mice, while minimizing systemic immunosuppression (as measured by MAHA response). We anticipate that we will find conditions for TRT administration and timing that can be combined with local xRT+IT-IC to the primary tumor that are as effective as our regimen of IT-IC to the primary tumor following xRT to both tumors (FIG. 3).

Testing the Efficacy of TRT+xRT+IT-IC in Mice Bearing More than Two B78 Tumors.

This section of Example 4 is most analogous to the relevant clinical setting; namely, patients with an injectable tumor that could be used as an in situ vaccine site, but with multiple distant metastases that could each be causing tumor-induced immune tolerance. These studies will replicate the conditions found to be most effective in the first part of Example 4 (above). The important difference is that these mice will each have four separate tumors, in L and R flanks, and L and R para-scapular regions. The TRT would be given at the dose and timing found most effective in the studies outlined in the first section of Example 4, with xRT+IT-IC subsequently given only to the L-flank lesion. The goal here is to test TRT dose and timing issues to enable an effective in situ vaccine to function, because the TRT would effectively eliminate the tumor-induced immune tolerance caused by the three sites not getting xRT. The measure of efficacy would be elimination of all four tumors in most mice. Modifications in TRT dose and timing will be studied in order to generate a regimen that is most effective. Such a regimen could then be considered for future translation to the clinic for patients with multiple distant metastases, that could not all be irradiated via external beam, but could be irradiated via TRT, when combined with local xRT+IT-IC to the "in situ vaccine" site.

Initiating Studies of TRT+xRT and IT-IC in Mice Bearing NXS2, 9464D-GD2 or Panc02-GD2 in Two or More Sites.

As in Examples 2 and 3, once the studies outlined in the previous sections of Example 4 are progressing, we will initiate similar studies in mice bearing NXS2, 9464D-GD2 or Panc02-GD2 in two or more sites.

Example 5: Experiments Determining the Dose of xRT Needed for Optimal In Situ Vaccine Effect to a Primary Tumor, and the Lowest Dose of xRT to a Distant Tumor Needed to Prevent Concomitant Immune Tolerance Dose titration experiments, evaluating a variety of xRT doses, to mice with 1 or 2 tumors have been performed. The first goal has been to test the dose of xRT needed in mice with one tumor to facilitate synergy and an "in situ vaccine" with IT-IC, tumor-reactive mAb linked to IL2. Initial experiments have confirmed our prior observation that 12 Gy RT alone does not eradicate or even regress the growth of established B78 melanoma tumors (0% complete regression), whereas 12 Gy+IT-IC results in complete regression of most B78 tumors (66%) in mice bearing a single tumor. On the other hand, 2 Gy+IT-IC slows tumor progression compared to IT-IC alone (mean tumor size day 32=472 mm$^3$ vs 1214 mm$^3$, respectively) but did not render any mice disease free (0% complete regression).

In our "2-tumor model", we have previously shown that treatment of one "primary" tumor with xRT+IT-IC is not effective in treating either the treated primary tumor or the untreated "secondary" tumor. In fact, in this 2-tumor model we have observed that the presence of the second tumor eliminates the efficacy of IT-IC injection following xRT. We have designated this phenomenon as "concomitant immune tolerance" (CIT), and demonstrated that this results, at least in part, from T regulatory cells (Tregs) in the distant (non-irradiated) secondary tumor, which circulate systemically and repopulate the xRT-treated/IT-IC injected primary tumor. These Tregs that return to the primary tumor appear to interfere with the desired "in situ vaccine" effect.

We have now confirmed our prior observation that CIT can be overcome by delivering 12 Gy xRT to both the primary and the secondary tumor. Importantly, given that Tregs are quite sensitive to RT, we hypothesized that a lower dose of RT could be delivered to the secondary tumor in order to overcome CIT and rescue response to in situ vaccination at the primary tumor (primary tumor treated with 12 Gy+IT-IC). We have now tested this and observed that xRT doses of 2 Gy or 5 Gy to the secondary tumor are comparable to 12 Gy in their capacity to blunt CIT and rescue response to primary tumor treatment with 12 Gy+IT-IC. These important experiments have been repeated in duplicate, and suggest (as hypothesized) that the dose of xRT that must be given to distant tumors to prevent CIT is much less than the dose needed at the IT-IC injected primary tumor site for the purpose of generating an in situ vaccine effect.

This supports our overarching hypothesis in this disclosure, and suggests that in animals bearing multiple tumors we will be able to deliver a relatively low dose of RT to all sites of disease using the targeted radiotherapeutic (TRT) NM404, and thereby overcome CIT when this is combined with local xRT and IT-IC injection of a single tumor site (the in situ vaccine site).

Example 6: Experiments Determining the $^{131}$I-NM404 Dosing that Approximates the Required Dosing of xRT to Metastases, as Determined Above, and then Evaluating the Effects of that $^{131}$I-NM404 Dose on In Vivo Immune Function Based on the preliminary data described above, studies have been done to move these concepts into in vivo testing using TRT. Dosimetry studies have been performed on mice bearing 1 or 2 B78 tumors (the tumor model that we have used to demonstrate best our in situ vaccine approach and the hurdle of CIT). This was done in order to estimate the amount of $^{131}$I-NM404 that would be needed to approximate ~2 Gy of xRT.

In order to then determine if a ~2 Gy equivalent dose of $^{131}$I-NM404 would have the desired effects against intratumor lymphoid cells (particularly Tregs), 2 separate approaches have been pursued. First, we administered this dose of $^{131}$I-NM404 to mice bearing a radiosensitive lymphoma tumor, which exhibits comparable NM404 uptake to B78 tumors. Following this we have documented potent lymphoid tumor shrinkage/dose-dependent inhibition under conditions that did not cause either substantial shrinkage/slowing of the B78 tumor or any evident depletion of circulating lymphoid cells (as gauged by peripheral complete blood counts). These data are consistent with the fact that lymphoid cells are much more sensitive to low-dose RT than are typical solid tumor cells, and suggest that selective uptake of TRT in tumor may enable intratumor lymphoid cell depletion without systemic lymphopenia. These studies also suggest that such a lymphoid tumor could serve as an in vivo biological "dosimeter" for identifying and monitoring the effect of TRT on intratumor lymphoid cells.

A second approach involved treating mice with B78 tumors with these same doses of $^{131}$I-NM404. These animals were then sacrificed at half-life (8 d) intervals, and after sufficient delay for radioactive decay, the tumors were stained for the presence of effector T cells and Tregs by immunohistochemistry Intriguingly, the animals receiving $^{131}$I-NM404 in this initial experiment showed no systemic lymphopenia at any time point (by peripheral complete blood count) but did show a decrease in intratumor FoxP3+ Tregs at 2 half-lifes following TRT administration. At this 2-half-life time point, we also observed a decrease in intratumor effector CD8+ T cells. Importantly, however at subsequent 3 and 4 half-life time points we observed an increase in intratumor CD8+ effector T cells but a further decline in the levels of intratumor Tregs, both compared to untreated baseline and $2^{nd}$ half-life levels. This observation again supports our hypothesis that it will be feasible to use TRT to overcome Treg-mediated CIT in order to rescue an in situ vaccine effect in animals bearing multiple tumors.

Finally, to characterizing the immunological effects of TRT on the immune cells within tumors, we have treated B78 bearing mice with $^{131}$I-NM404 and collected tumor tissue at pretreatment and at half-life (8 d) intervals thereafter. These tissues were then analyzed by RT-PCR for gene expression of a panel of immune signatures. The results indicate that TRT treatment alone causes striking changes in expression of tumor cell markers of immunsusceptibility and in genes normally expressed only by immune cells, with the latter showing a clear time course of decreased expression followed by rebound over-expression.

Example 7: Experiments Using Data from Examples 5 and 6 to Develop a Regimen of $^{131}$I-NM404+Local xRT+IT-mAb/IL2 in Mice Bearing Two or More Tumors and Induce T-Cell Mediated Eradication of all Distant Tumors This Example illustrates treating animals bearing tumors in at least 2 locations. Our strategy involves using xRT and local IT-IC at the in situ vaccine site, in combination with TRT systemically to inhibit CIT, in order to obtain enhanced anti-tumor immune activity at all tumor sites. Critical issues of TRT and xRT dose and timing will be optimized for antitumor efficacy.

Using the data summarized in Examples 5 and 6, a study was done in mice bearing 2 separate B78 tumors. Mice received the estimated required systemic 131I-NM404 dose followed by xRT and local immunotherapy to the in situ vaccine site. With appropriate controls, this dose of $^{131}$I-NM404 did appear to attenuate CIT, as desired in mice with 2 tumors. In addition, in mice with one tumor, this TRT dose did not appear to interfere with the local in situ vaccine effect (as hypothesized and desired). Further testing, and modification of some of the experimental variables, is underway in order to try to maximize the desired effect of blocking CIT without suppressing the in situ vaccine effect. More details regarding these experiments are disclosed in Example 8 below.

Example 8: Data from Mice Bearing Two or More Tumors

Tumor-Specific Inhibition of Primary Tumor Response to the Combination of Local xRT+IT-IC by a Distant Untreated Tumor in Murine Melanoma and Pancreatic Tumor Models.

C57BL/6 mice bearing a syngeneic, GD2+ primary flank tumor+/−a secondary tumor on the contralateral flank were treated to the primary tumor only, as indicated, with xRT on day "1" and IT injection of 50 mcg of the anti-GD2 IC, hu14.18-IL2 on day 6-10.

Figure 7A:
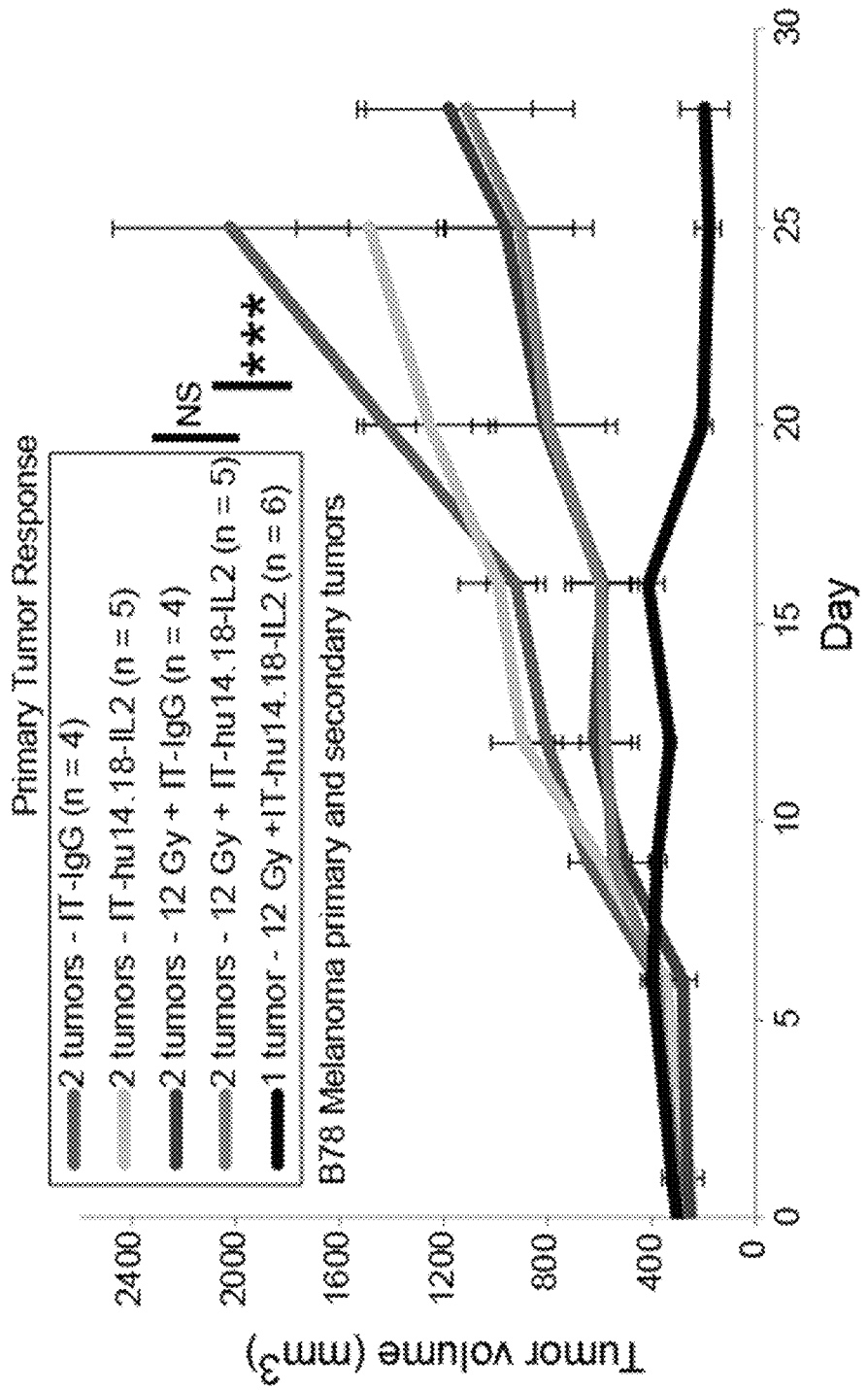
FIGS. 7A, 7B, 7C, 7D and 7E are a series of graphs showing tumor-specific inhibition of primary tumor response to the combination of local RT+IT-IC by a distant untreated tumor in murine melanoma and pancreatic tumor models. C57BL/6 mice bearing a syngeneic, disialoganglioside-expressing (GD2+), primary flank tumor+/−a secondary tumor on the contralateral flank were treated to the primary tumor only, as indicated, with xRT on day "1" and intra-tumor (IT) injection of 50 mcg of the anti-GD2 immunocytokine (IC), hu14.18-IL2 (a fusion of anti-GD2 mAb and IL2), on day 6-10. Mean primary tumor volumes are displayed in FIGS. 7A and 7C-7E. 7A). In mice bearing a primary B78 melanoma tumor, the presence of an untreated secondary B78 tumor antagonized primary tumor response to RT+IT-IC. We describe this effect as "concomitant immune tolerance"—an antagonistic effect of a non-treated distant tumor on the local response of a treated tumor to xRT+IT-IC. 7B) Kaplan-Meier survival curves are shown for mice in panel A plus replicate experiments. Nearly all mice were euthanized due to primary tumor progression. 7C) In mice bearing a primary Panc02-GD2+ pancreatic tumor, with or without a secondary Panc02-GD2− tumor on the opposite flank, the presence of an untreated Panc02 secondary tumor suppressed the response of a primary Panc02-GD2+ tumor to RT+IT-IC. 7D) In mice bearing a primary B78 melanoma tumor, a secondary B78 tumor suppressed primary tumor response to RT+IT-IC but a secondary Panc02-GD2+ pancreatic tumor did not exert this effect. 7E) In mice bearing a primary Panc02-GD2+ tumor a secondary Panc02-GD2− tumor suppressed primary tumor response to combined xRT and IT-hu14.18-IL2, while a B78 secondary tumor did not. n=number of mice per group. NS=non-significant, ***p<0.001.
Figure 7B:
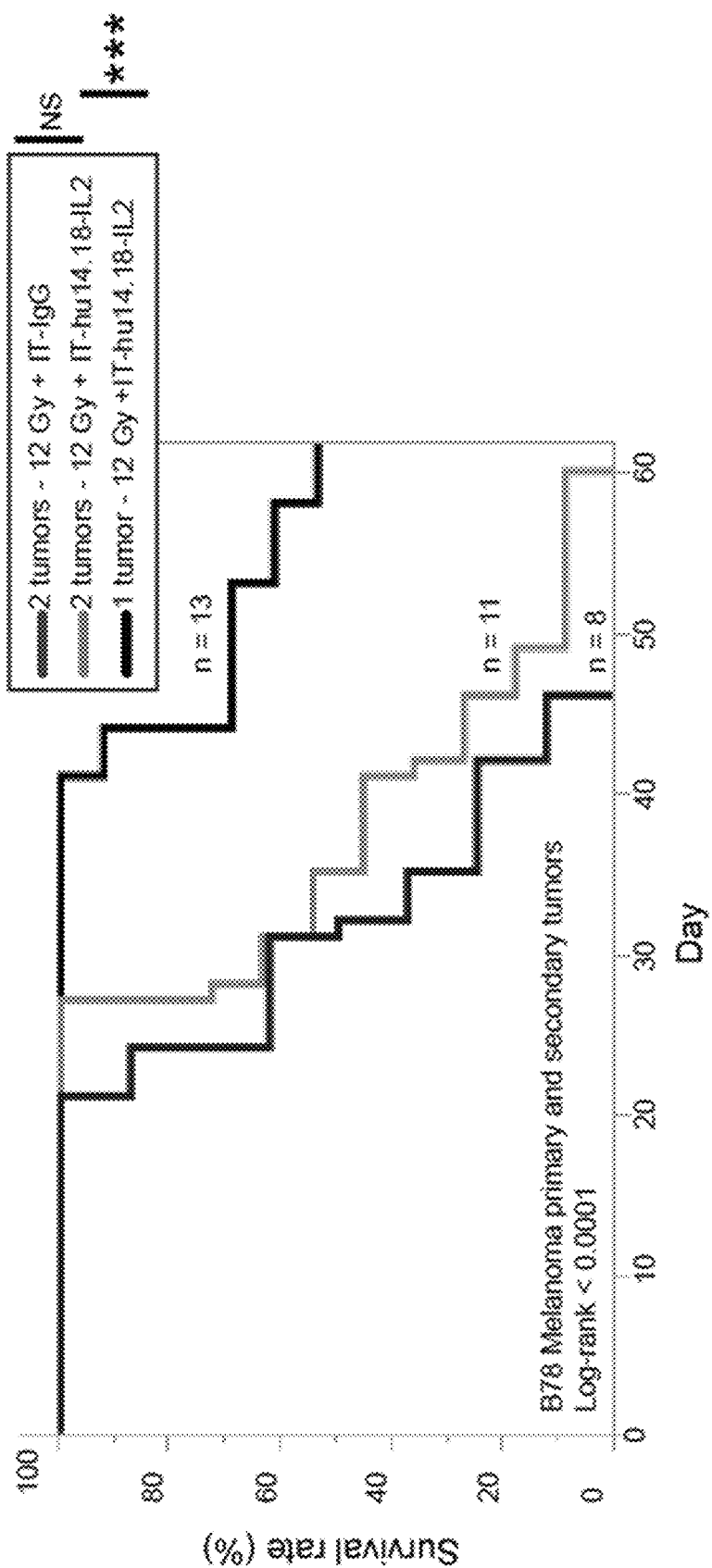

In mice bearing a primary B78 melanoma tumor, the presence of an untreated secondary B78 tumor antagonized primary tumor response to xRT+IT-IC (FIG. 7A). We describe this effect as "concomitant immune tolerance"—an antagonistic effect of a non-treated distant tumor on the local response of a treated tumor to xRT+IT-IC. Kaplan-Meier survival curves were obtained for these mice plus replicate experiments (FIG. 7B). Nearly all mice were euthanized due to primary tumor progression.

Figure 7C:
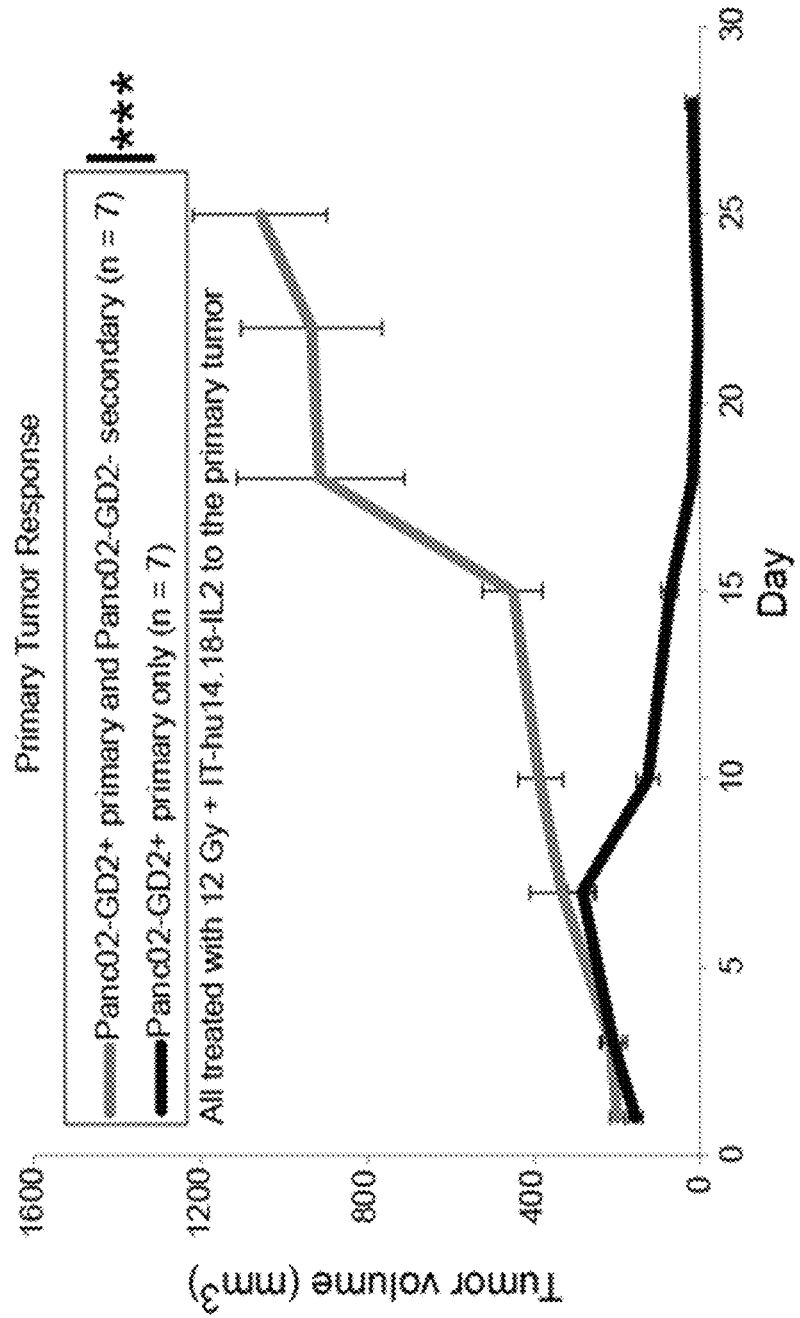
Figure 7D:
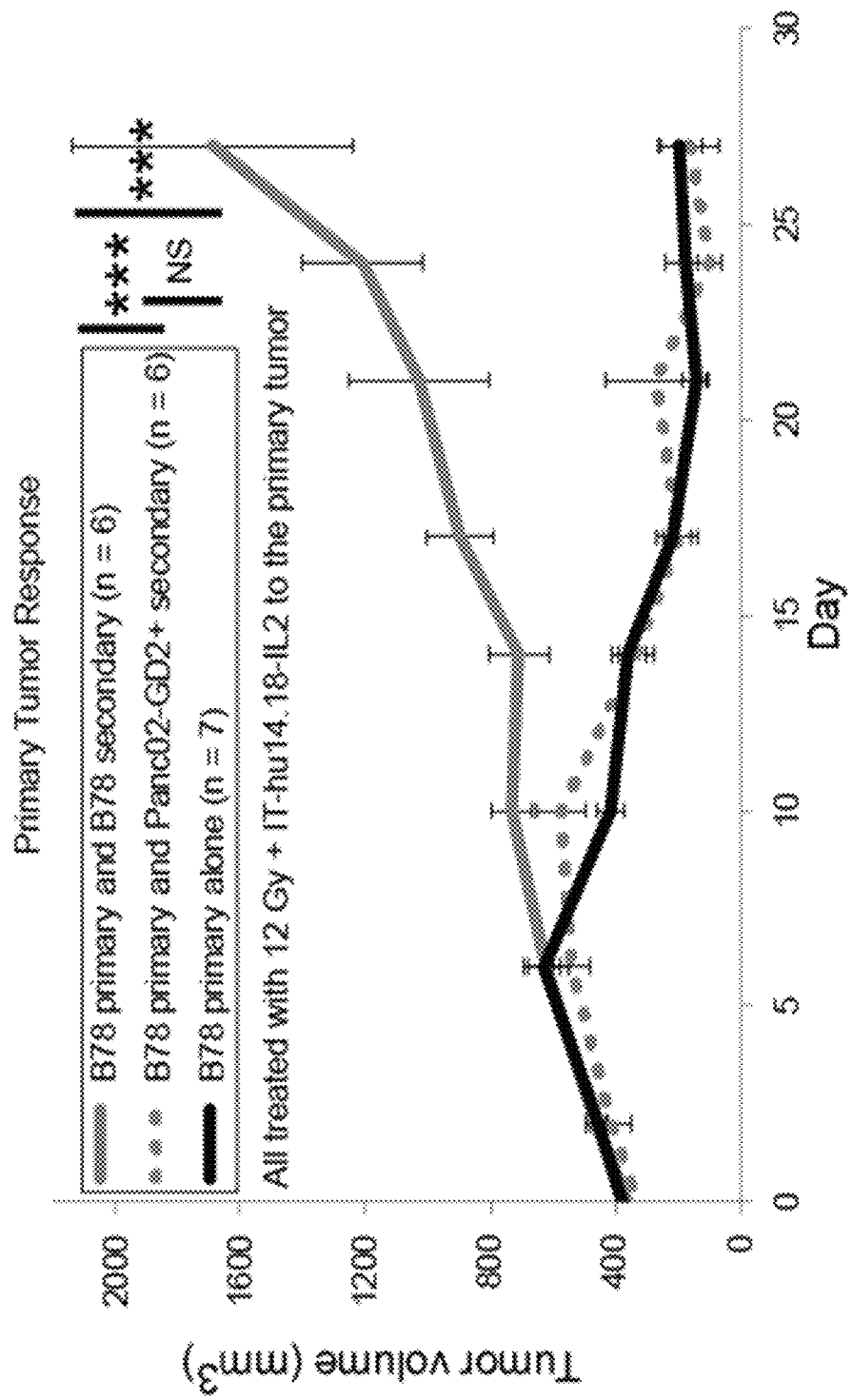
Figure 7E:
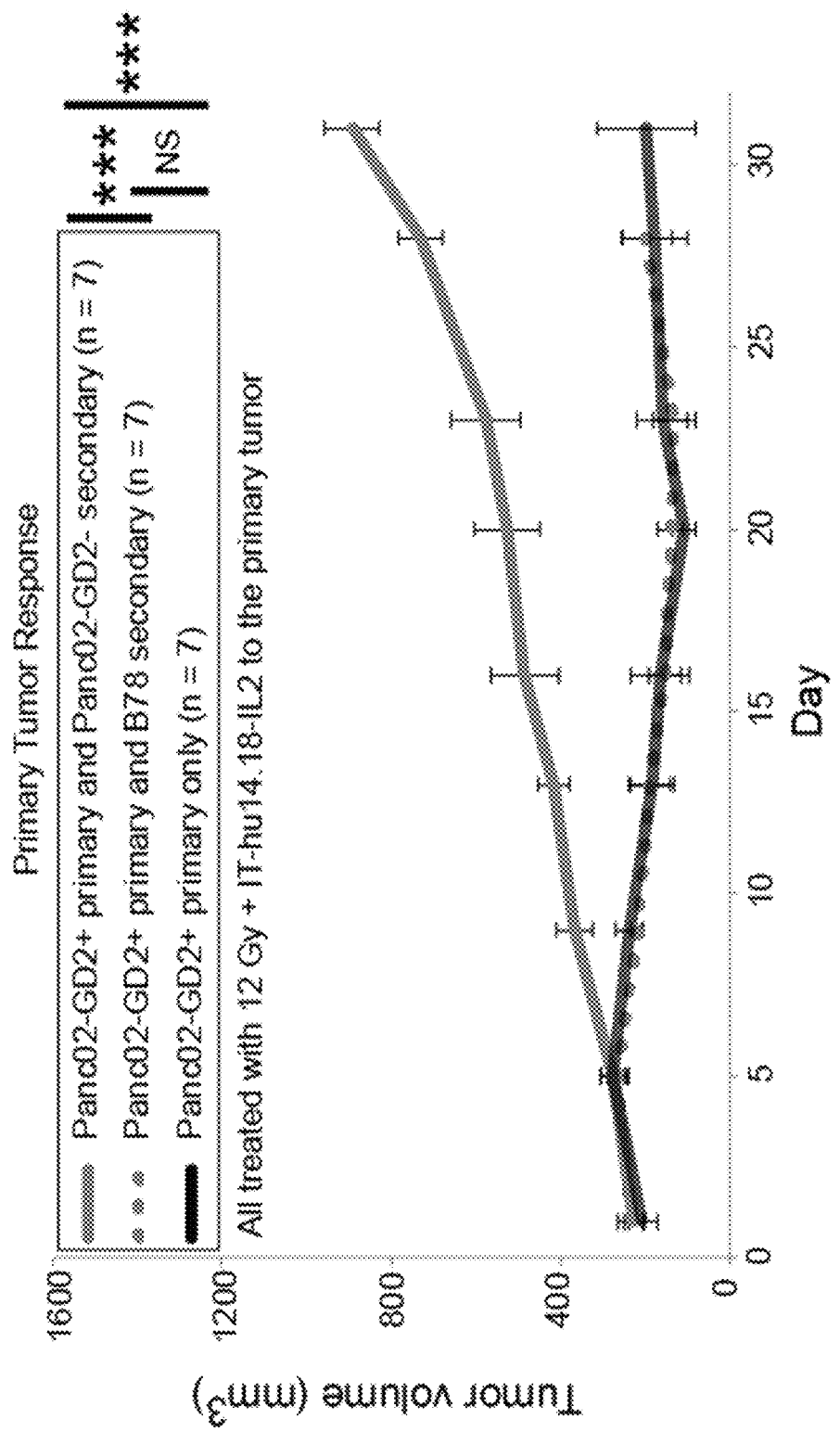

In mice bearing a primary Panc02-GD2+ pancreatic tumor, with or without a secondary Panc02-GD2− tumor on the opposite flank, the presence of an untreated Panc02 secondary tumor suppressed the response of a primary Panc02-GD2+ tumor to xRT+IT-IC (FIG. 7C). In mice bearing a primary B78 melanoma tumor, a secondary B78 tumor suppressed primary tumor response to xRT+IT-IC but a secondary Panc02-GD2+ pancreatic tumor did not exert this effect (FIG. 7D). In mice bearing a primary Panc02-GD2+ tumor a secondary Panc02-GD2− tumor suppressed primary tumor response to combined xRT and IT-hu14.18-IL2, while a B78 secondary tumor did not FIG. 7E).

Concomitant Immune Tolerance is Circumvented by Specific Depletion of Regulator T Cells (Tregs).

Figure 8A:
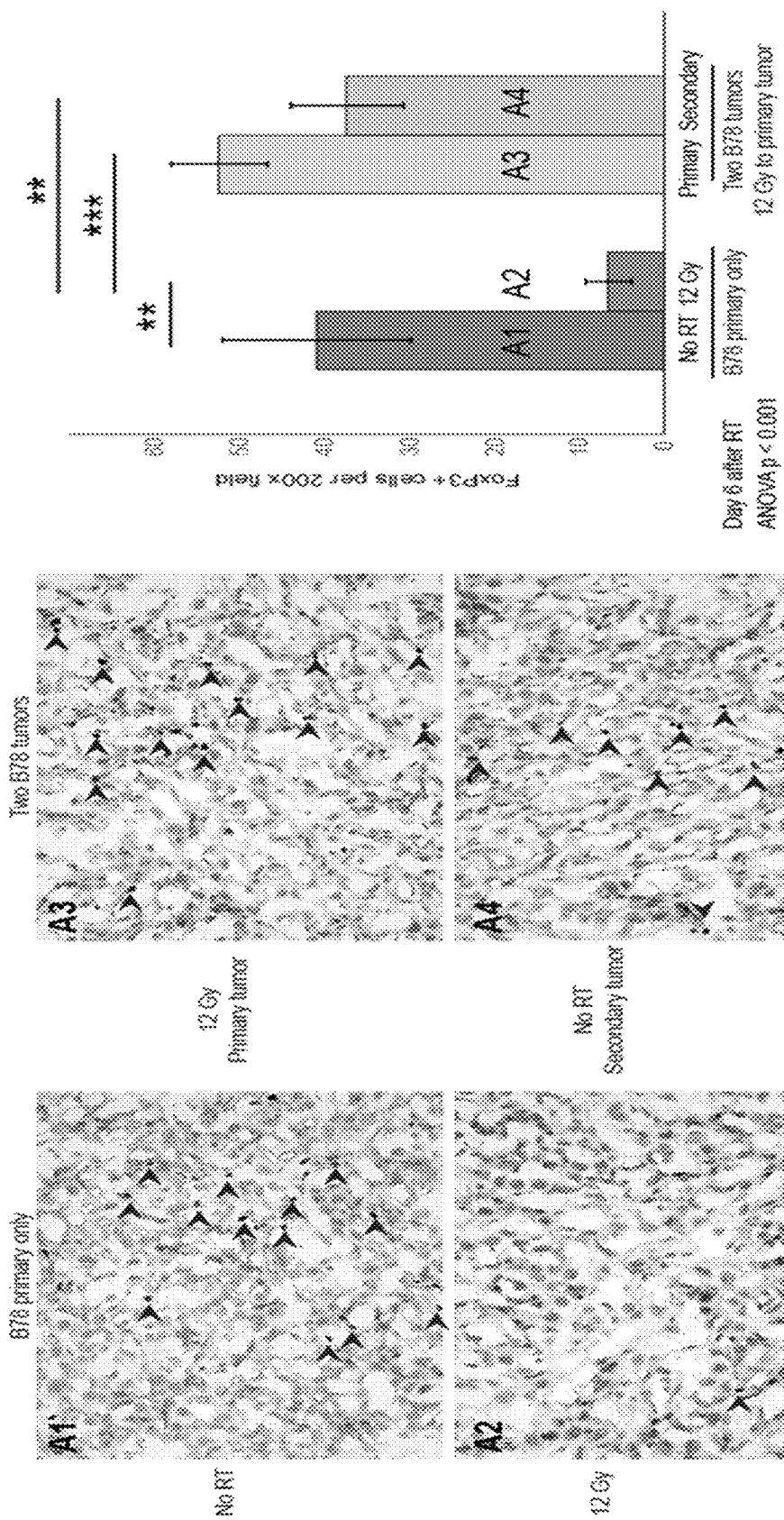
FIGS. 8A, 8B and 8C include immunohistochemistry images and graphs showing that concomitant immune tolerance is circumvented by specific depletion of regulator T cells (Tregs). 8A). Immunohistochemistry for the Treg marker, FoxP3 (representative 400× images are shown) for tumors evaluated on day 6 after xRT in mice with one (A1 and A2) or two (A3 and A4) tumors. Mice received no xRT, or xRT only to the primary tumor. The primary tumor is shown in A1-A3 and the secondary is shown in A4. Small arrows point out some of the FoxP3+ cells (brown nuclei=FoxP3+, blue=hematoxylin counterstain). The graphs on the right display blinded quantification of FoxP3+ cells per 200× field, corresponding to the conditions shown in A1, A2, A3 and A4, respectively. 8B and 8C) DEREG mice express diphtheria toxin receptor under control of the Treg-specific FoxP3 promoter, enabling specific depletion of Tregs upon IP injection of diphtheria toxin. DEREG mice bearing primary and secondary B78 melanoma tumors were treated with xRT+IT-IC to the primary tumor and IP injection of either diphtheria toxin or PBS (the first of replicate experiments are shown). Concomitant immune tolerance is eliminated following depletion of Tregs in these mice, resulting in improved 8B) primary and 8C) secondary tumor response. n=number of mice per group. p<0.01, *p<0.001.
Figure 8B:
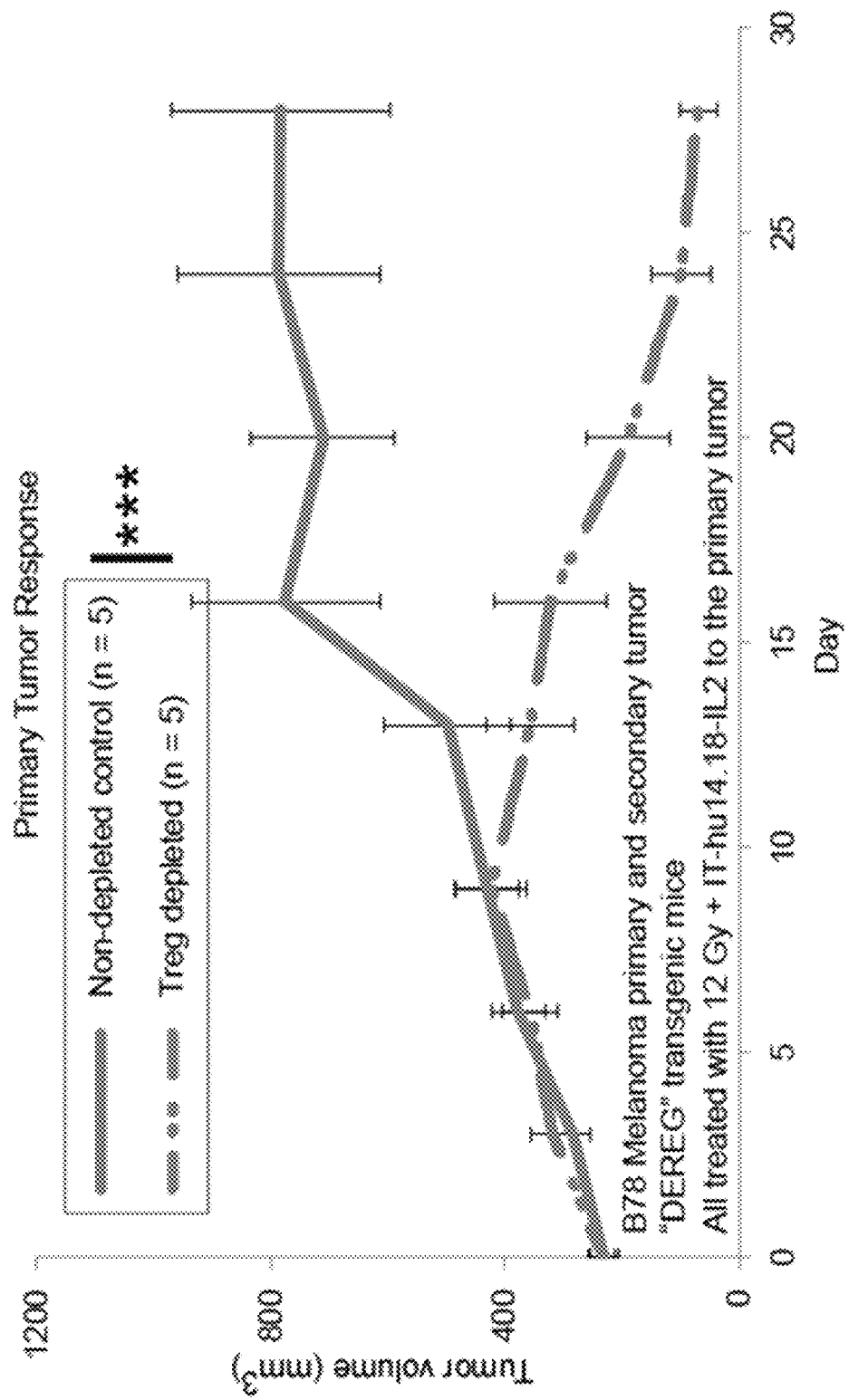
Figure 8C:
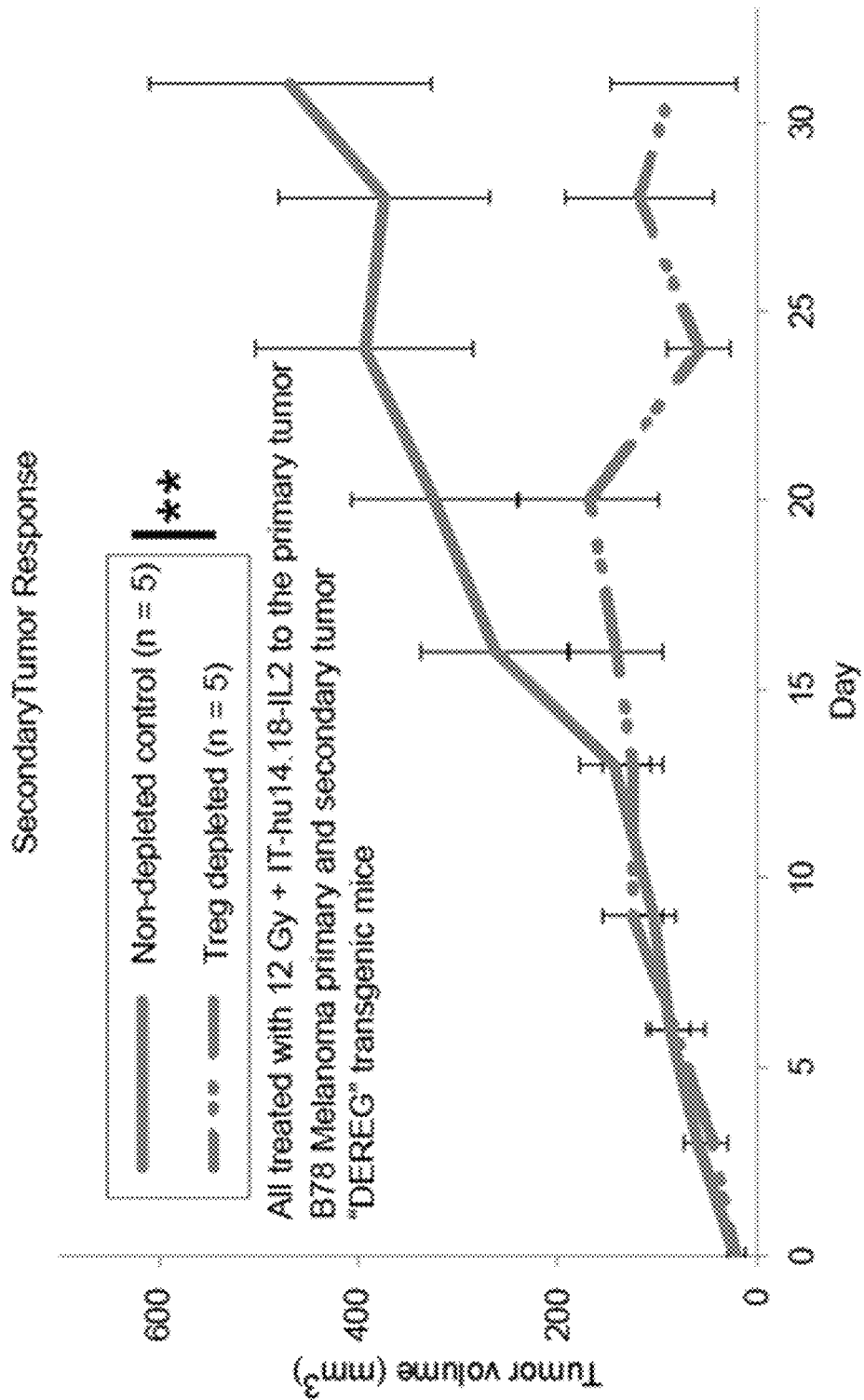

Immunohistochemistry images were obtained for the Treg marker, FoxP3 for tumors evaluated on day 6 after xRT in mice with one or two tumors (FIG. 8A). Mice received no xRT, or xRT only to the primary tumor. DEREG mice express diphtheria toxin receptor under control of the Treg-specific FoxP3 promoter, enabling specific depletion of Tregs upon IP injection of diphtheria toxin (FIGS. 8B and 8C). DEREG mice bearing primary and secondary B78 melanoma tumors were treated with xRT+IT-IC to the primary tumor and IP injection of either diphtheria toxin or PBS. Concomitant immune tolerance is eliminated following depletion of Tregs in these mice, resulting in improved primary (FIG. 8B) and secondary (FIG. 8C) tumor response.

Concomitant Immune Tolerance is Overcome by Delivering xRT to Both Tumor Sites.

Figure 9A:
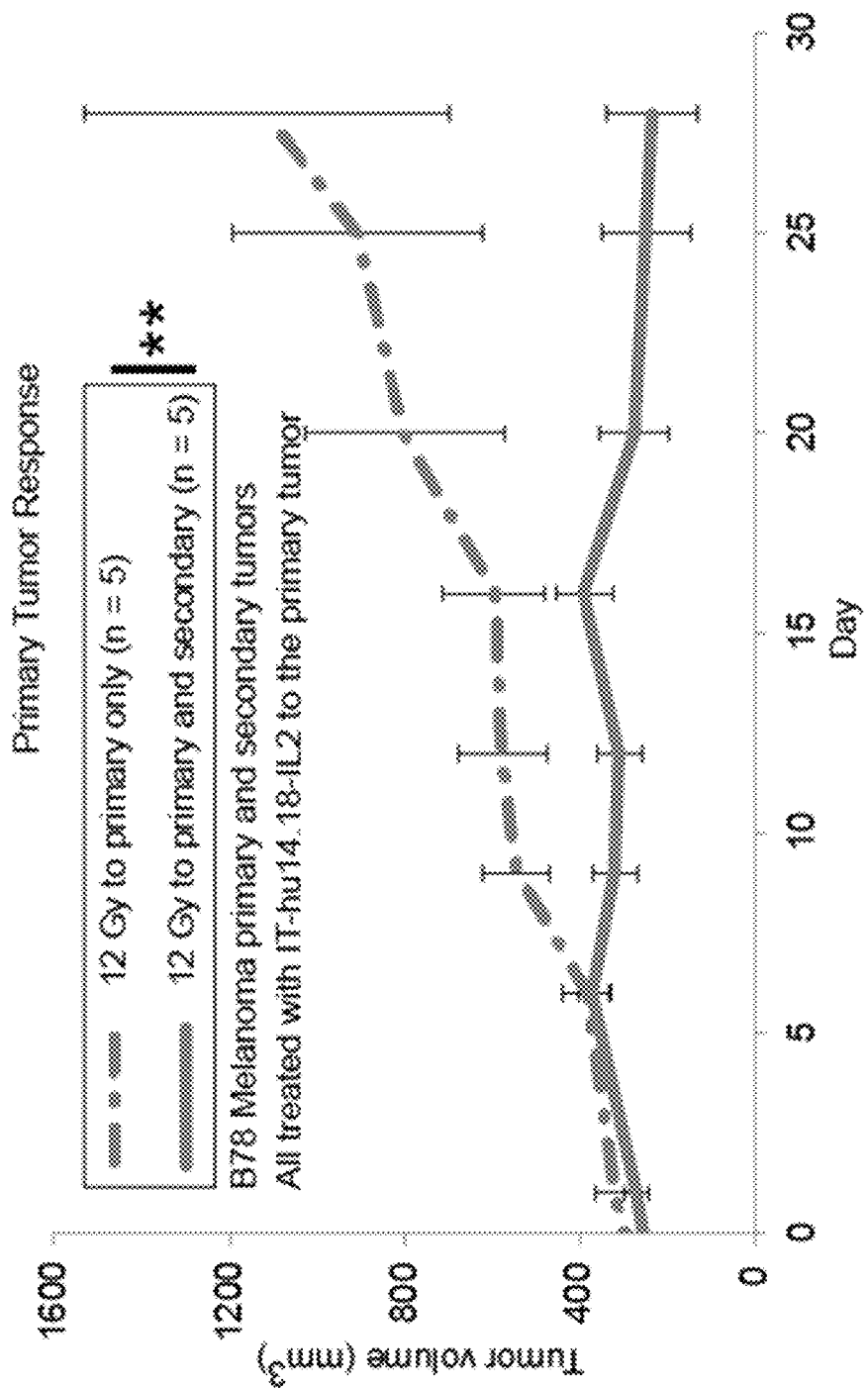
FIGS. 9A and 9B are graphs showing that concomitant immune tolerance is overcome by delivering xRT to both tumor sites. In mice bearing primary and secondary B78 tumors, the secondary tumor suppresses primary tumor response to primary tumor treatment with xRT+IT-IC. This is overcome by delivering 12 Gy xRT to both the primary and secondary tumors and IT-IC to the primary tumor, resulting in improved 9A) primary tumor response (the first of replicate experiments is shown) and 9B) aggregate animal survival from replicate experiments. n=number of mice per group. p<0.01, *p<0.001.
Figure 9B:
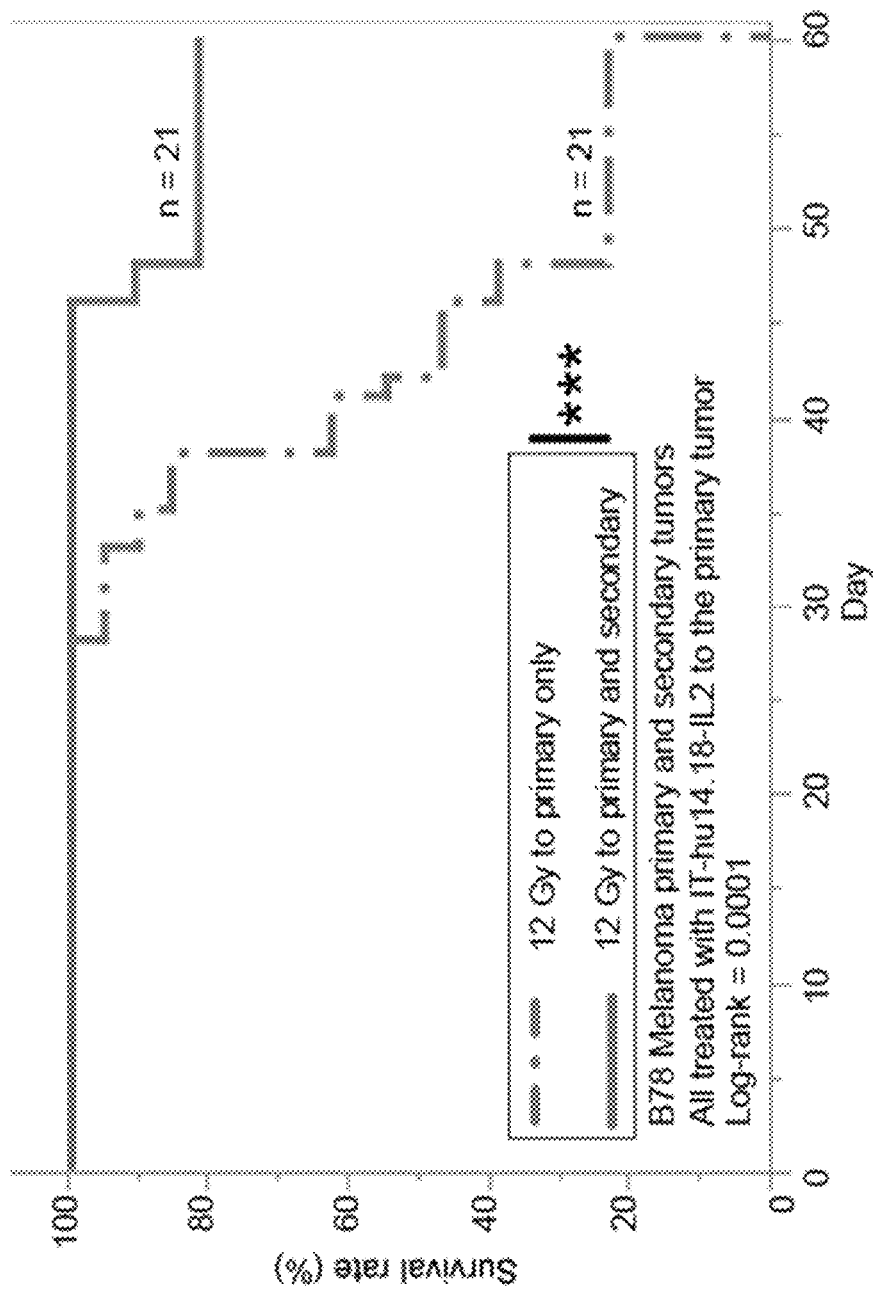

In mice bearing primary and secondary B78 tumors, the secondary tumor suppresses primary tumor response to primary tumor treatment with xRT+IT-IC. This is overcome by delivering 12 Gy xRT to both the primary and secondary tumors and IT-IC to the primary tumor, resulting in improved primary tumor response (FIG. 9A) and aggregate animal survival (FIG. 9B) from replicate experiments.

Low Dose xRT Alone does not Elicit In Situ Vaccination but does Overcome Concomitant Immune Tolerance when Delivered to Distant Tumor Sites Together with 12 Gy+IT-IC Treatment of an In Situ Vaccine Site.

Figure 10A:
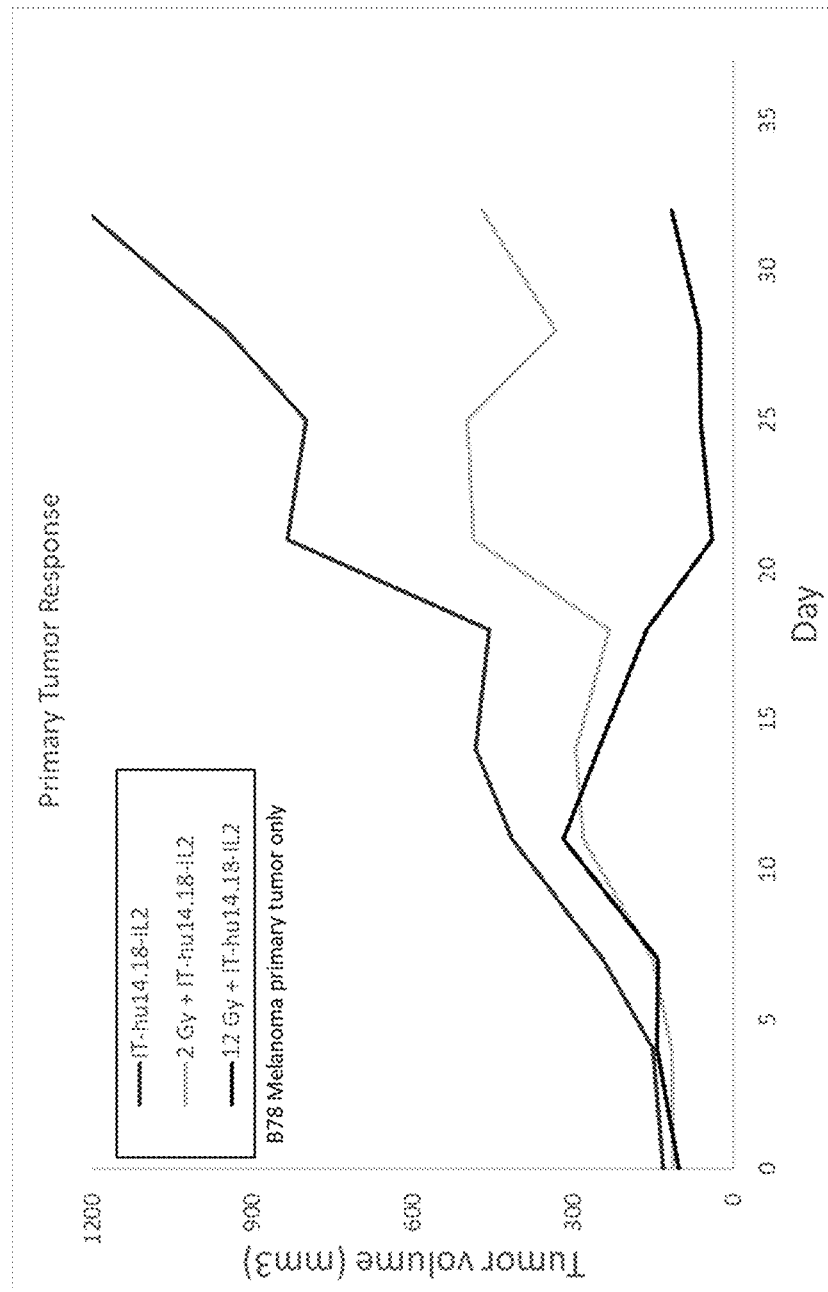
FIGS. 10A, 10B and 10C are a series of graphs showing that low dose xRT alone does not elicit in situ vaccination but does overcome concomitant immune tolerance when delivered to distant tumor sites together with 12 Gy+IT-IC treatment of an in situ vaccine site. 10A) In mice bearing a primary B78 tumor only, 12 Gy+IT-IC elicits in situ vaccination (as shown previously) and results in complete tumor regression in most mice (4/6 in this experiment) and a memory immune response (Morris, Cancer Res, 2016). On the other hand no animals exhibit complete tumor regression following either IT-IC alone or low dose (2 Gy) xRT+IT-IC (0/6 in both groups) p<0.05. 10B) In mice bearing a primary and secondary B78 melanoma tumor, low dose xRT (2 Gy or 5 Gy) delivered to the secondary tumor is comparable to 12 Gy in its capacity to overcome concomitant immune tolerance at the primary tumor. 10C) In these same animals, it is apparent that overcoming concomitant immune tolerance by delivery of low dose xRT to the secondary tumor rescues a systemic response to IT-IC immunotherapy. In this context, when xRT is delivered to all tumor sites then IT-IC injection of the primary tumor triggers a systemic anti-tumor effect that renders secondary tumor response to 2 Gy or 5 Gy greater than the response to 12 Gy xRT in absence of primary tumor IT-IC injection.

In mice bearing a primary B78 tumor only, 12 Gy+IT-IC elicits in situ vaccination (as shown previously) and results in complete tumor regression in most mice (FIG. 10A) and a memory immune response (Morris, Cancer Res, 2016). On the other hand no animals exhibit complete tumor regression following either IT-IC alone or low dose (2 Gy) xRT+IT-IC (0/6 in both groups) p<0.05.

Figure 10B:
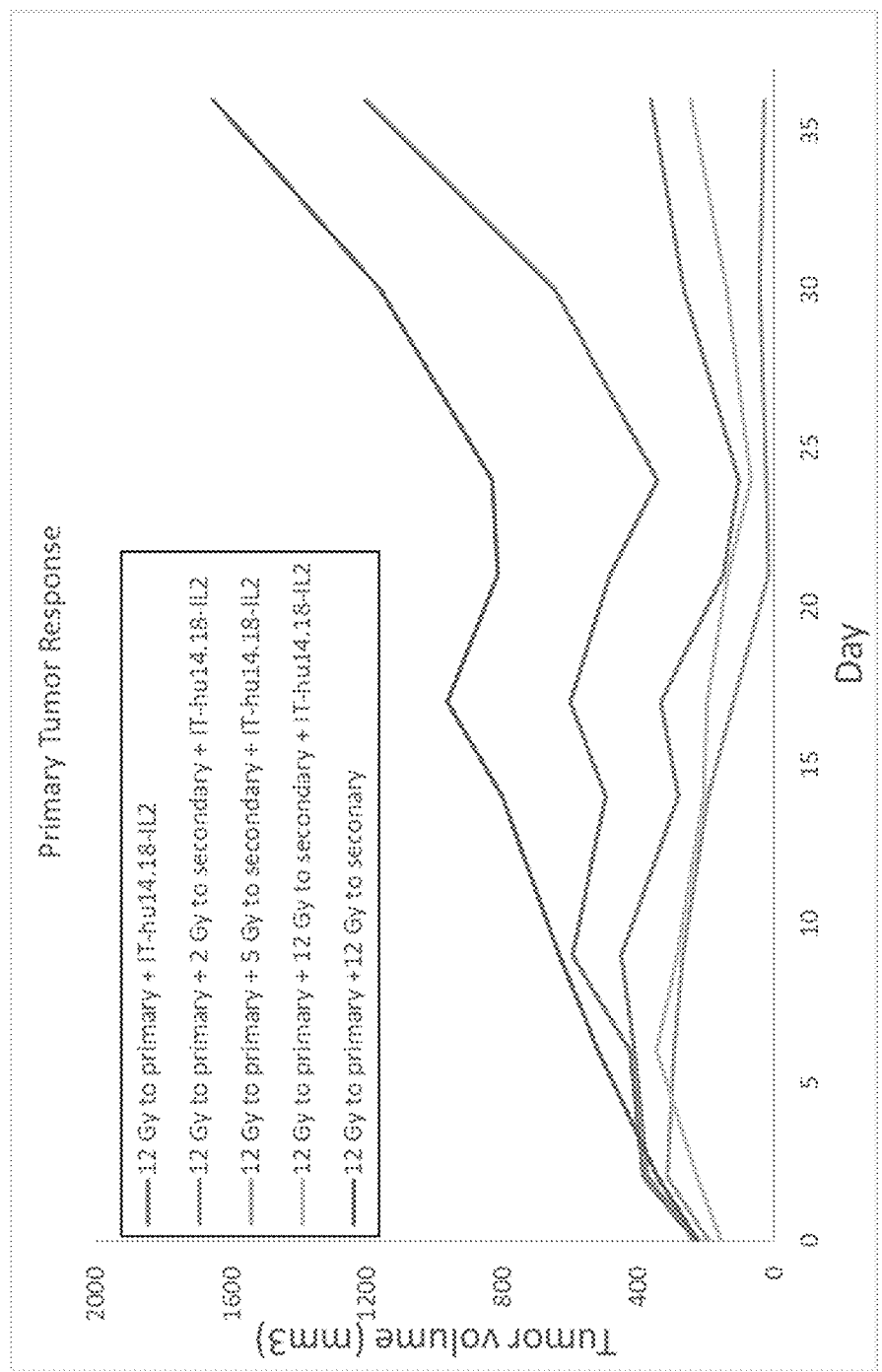
Figure 10C:
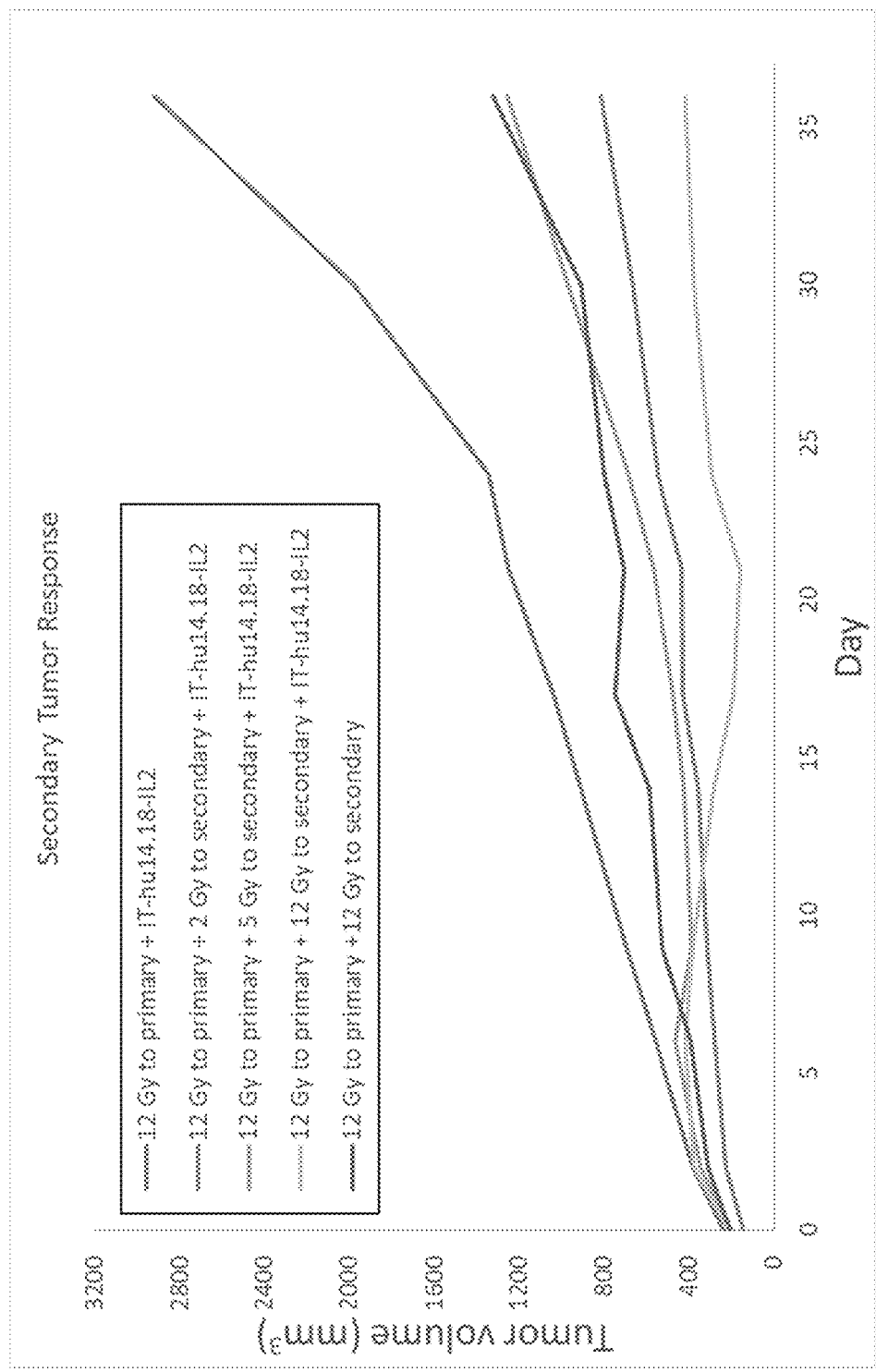

In mice bearing a primary and secondary B78 melanoma tumor, low dose xRT (2 Gy or 5 Gy) delivered to the secondary tumor is comparable to 12 Gy in its capacity to overcome concomitant immune tolerance at the primary tumor (FIG. 10B). In these same animals, it is apparent that overcoming concomitant immune tolerance by delivery of low dose xRT to the secondary tumor rescues a systemic response to IT-IC immunotherapy (FIG. 0C). In this context, when RT is delivered to all tumor sites then IT-IC injection of the primary tumor triggers a systemic anti-tumor effect that renders secondary tumor response to 2 Gy or 5 Gy greater than the response to 12 Gy RT in absence of primary tumor IT-IC injection.

Low Dose TRT with $^{131}$I-NM404 Effectively Depletes Tumor Infiltrating FoxP3+ Tregs without Systemic Leukopenia or Depletion of Tumor Infiltrating CD8+ Effector T Cells.

Figure 11A:
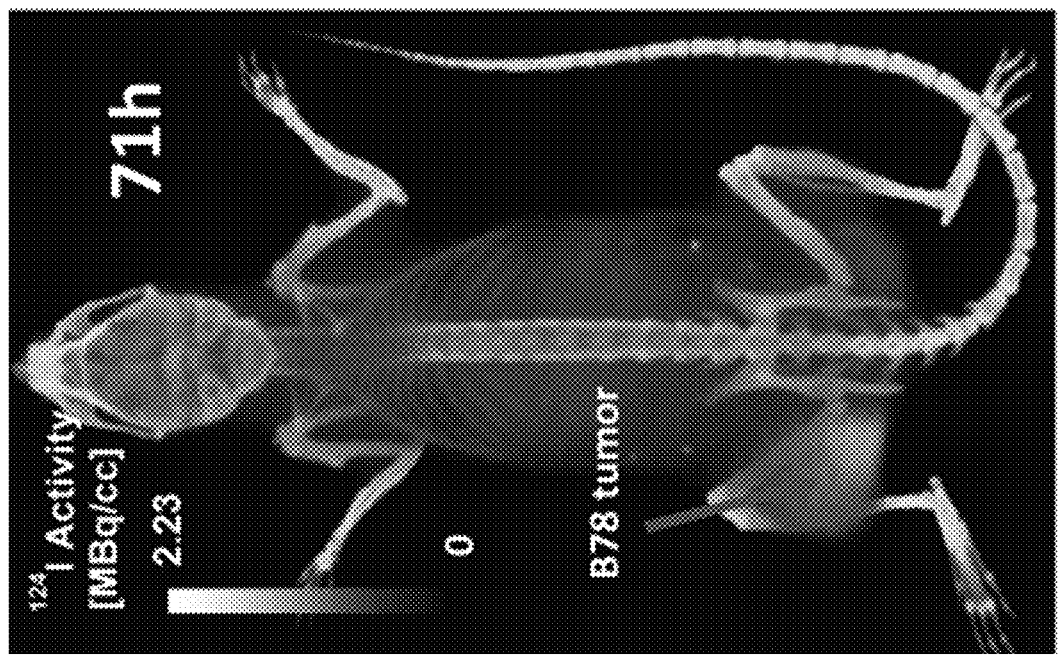
FIGS. 11A, 11B, 11C and 11D is a PET image (11A) and a series of bar graphs (11B, 11C and 11D) showing that low dose TRT with $^{131}$I-NM404 effectively depletes tumor infiltrating FoxP3+ Tregs without systemic leukopenia or depletion of tumor infiltrating CD8+ effector T cells. In most clinical scenarios, it is not feasible to deliver external beam, even low dose, to all tumor sites without eliciting marked bone marrow depletion and leukopenia that would result in immunosuppression. Here we tested whether TRT could be administered systemically to specifically deplete tumor infiltrating suppressive immune cells (Tregs), without triggering systemic immune cell depletion and leukopenia. 11A) Dosimetry studies in this B78 melanoma tumor model using positron-emitting $^{124}$I-NM404 confirm tumor-selective uptake of NM404. C57BL/6 mice bearing B78 tumors were treated with 60 µCi $^{131}$I-NM404. This activity approximates the amount of $^{131}$I-NM404 necessary to deliver ~2 Gy TRT to a B78 tumor. Peripheral blood and tumor samples were collected in untreated control mice (C) and at 8 day intervals (T1=d8, T2=d16, T3=d24, T4=d32) thereafter. 11B) This dose of TRT did not result in any significant systemic leukopenia and 11C) did not significantly affect the level of tumor infiltrating CD8+ effector T cells (ANOVA p=0.25). 11D) However, tumor infiltrating FoxP3+ Tregs were significantly depleted by this dose of TRT (ANOVA p=0.03; * p<0.05).
Figure 11B:
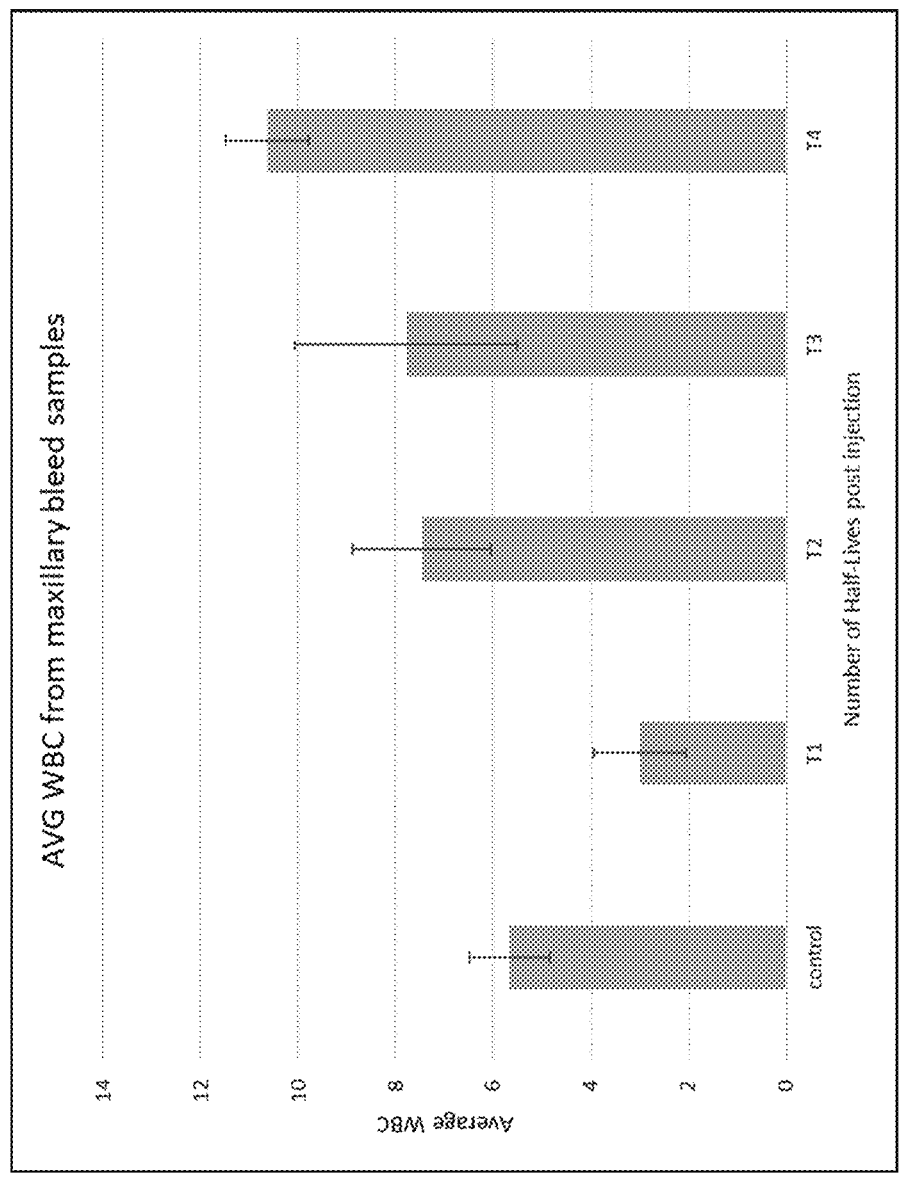
Figure 11C:
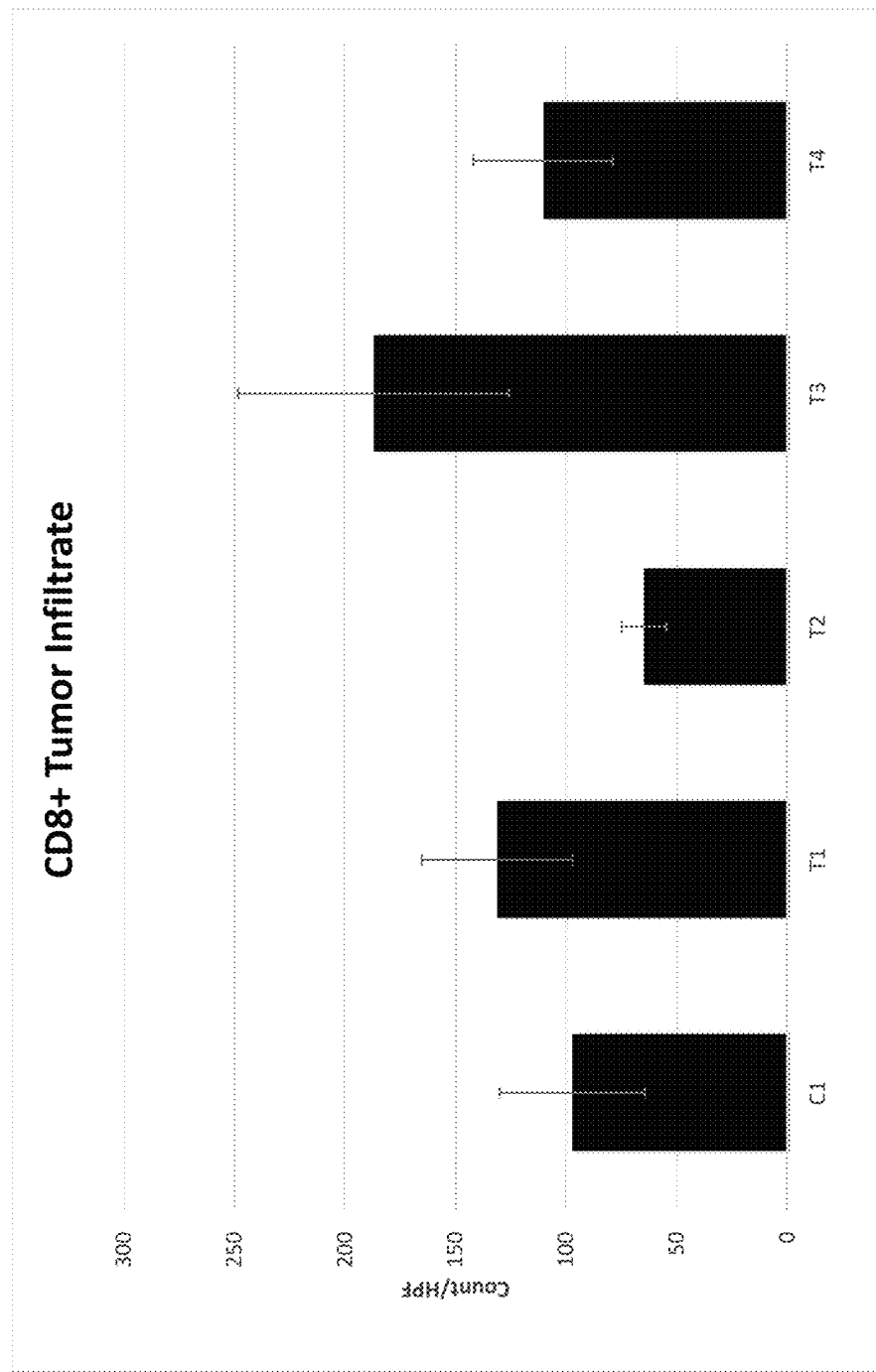
Figure 11D:
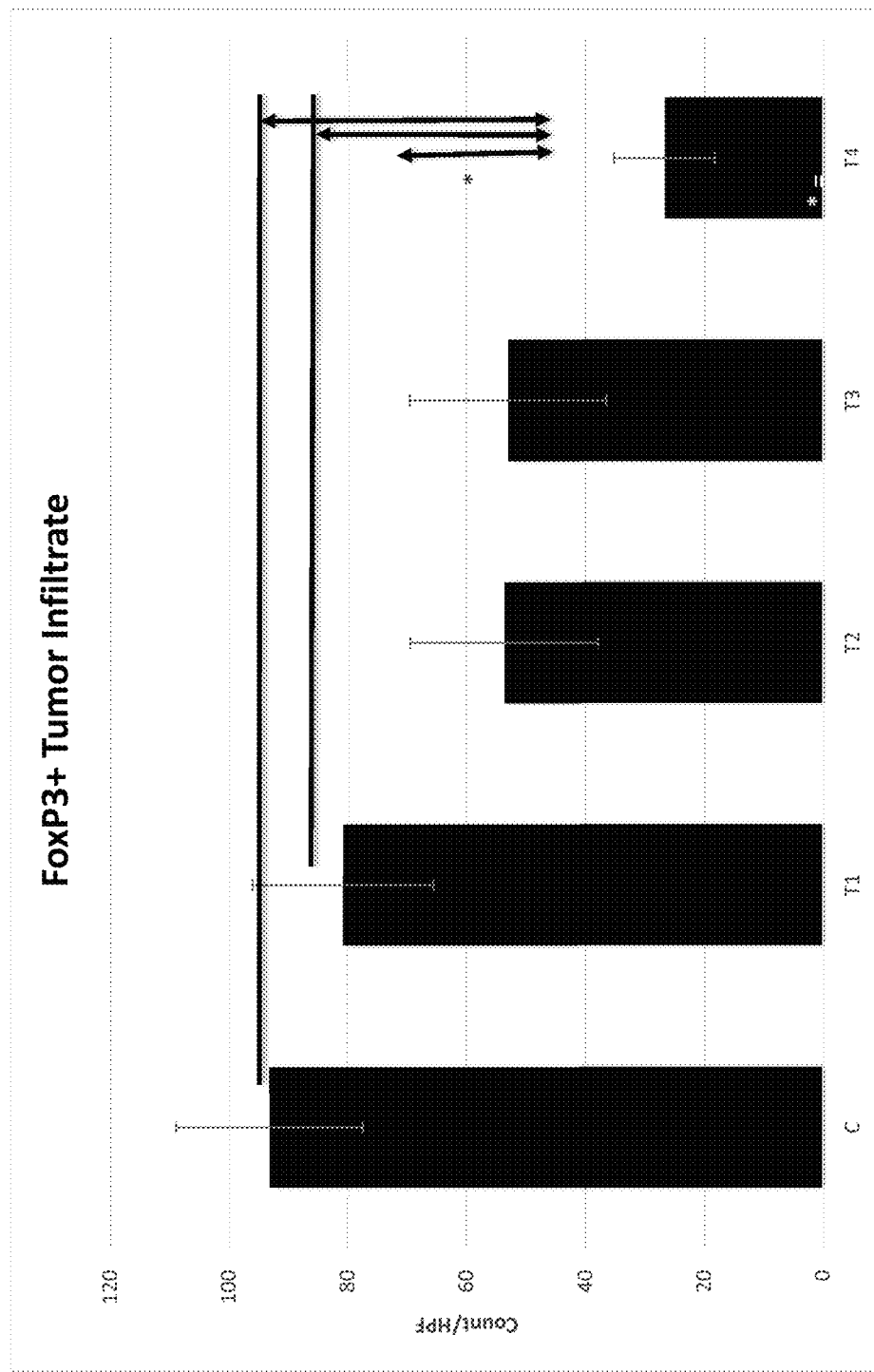

In most clinical scenarios, it is not feasible to deliver external beam, even low dose, to all tumor sites without eliciting marked bone marrow depletion and leukopenia that would result in immunosuppression. Here we tested whether TRT could be administered systemically to specifically deplete tumor infiltrating suppressive immune cells (Tregs), without triggering systemic immune cell depletion and leukopenia. Dosimetry studies in this B78 melanoma tumor model were performed using positron-emitting $^{4}$I-NM404 confirm tumor-selective uptake of NM404 (FIG. 11A). C57BL/6 mice bearing B78 tumors were treated with 60 µCi $^{131}$I-NM404. This activity approximates the amount of $^{131}$I-NM404 necessary to deliver ~2 Gy TRT to a B78 tumor. Peripheral blood and tumor samples were collected in untreated control mice (C) and at 8 day intervals (T1=d8, T2=d16, T3=d24, T4=d32) thereafter. This dose of TRT did not result in any significant systemic leukopenia (FIG. 11B) and did not significantly affect the level of tumor infiltrating CD8+ effector T cells (FIG. 11C). However, tumor infiltrating FoxP3+ Tregs were significantly depleted by this dose of TRT (FIG. 11D).

Low Dose TRT with $^3$I-NM404 Effectively Overcomes Concomitant Immune Tolerance and Rescues the Systemic Anti-Tumor Effect of In Situ Vaccination.

Figure 12A:
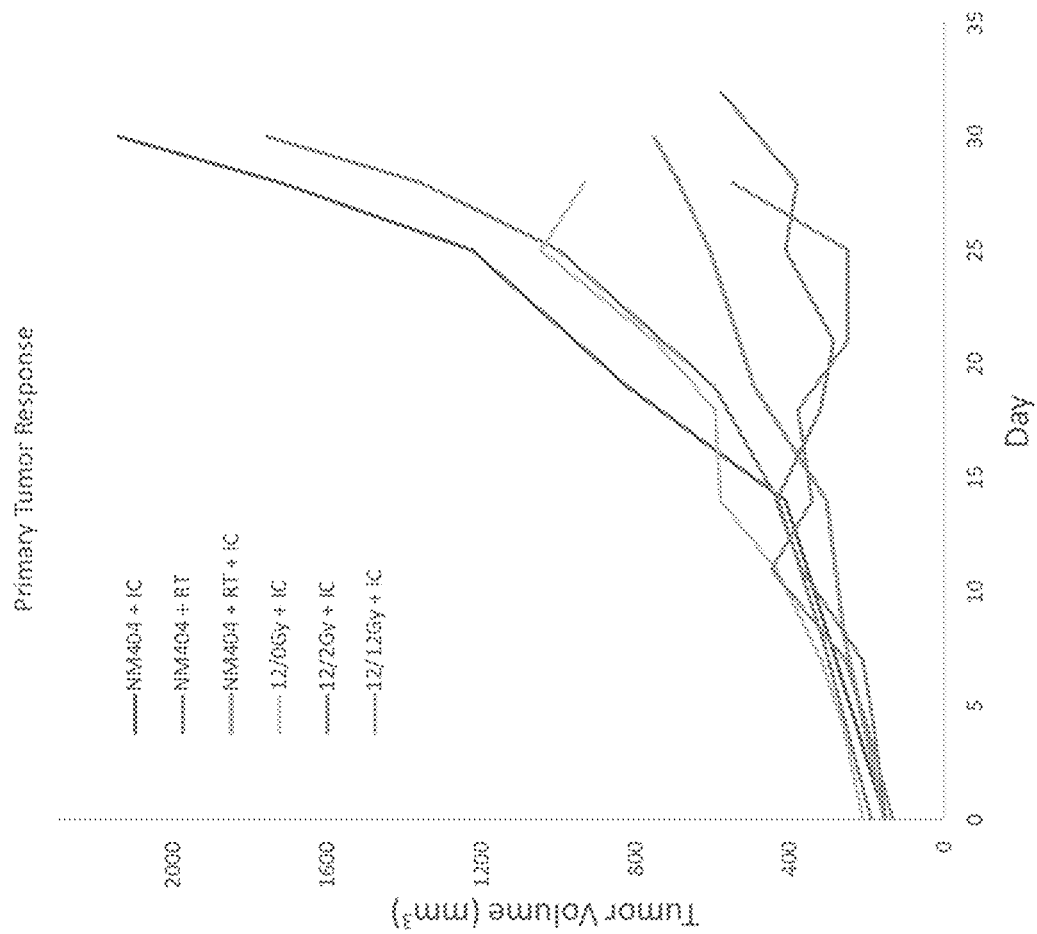
FIGS. 12A and 12B are graphs showing that low dose TRT with $^{131}$I-NM404 effectively overcomes concomitant immune tolerance and rescues the systemic anti-tumor effect of in situ vaccination. Given the capacity of low dose $^{131}$I-NM404 TRT to deplete tumor-infiltrating Tregs without rendering a mouse leukopenic, we tested whether low dose $^{131}$I-NM404 might effectively overcome concomitant immune tolerance. C57BL/6 mice bearing two B78 tumors were treated with 60-mcCi $^{131}$I-NM404 on day 1 (NM404), as indicated. After one half-life (day 8), animals received 12 Gy xRT or no xRT to the primary tumor (in situ vaccine site). Control mice receiving no $^{131}$I-NM404 were treated to the secondary tumor as indicated (0, 2, or 12 Gy). Mice received daily IT injections of IC to the primary tumor (in situ vaccine site), as indicated, on days 13-17. 12A) Primary tumor and 12B) secondary tumor response is shown and demonstrates that administration of low dose TRT effectively overcomes concomitant immune tolerance and rescues the systemic anti-tumor effect of in situ vaccination.
Figure 12B:
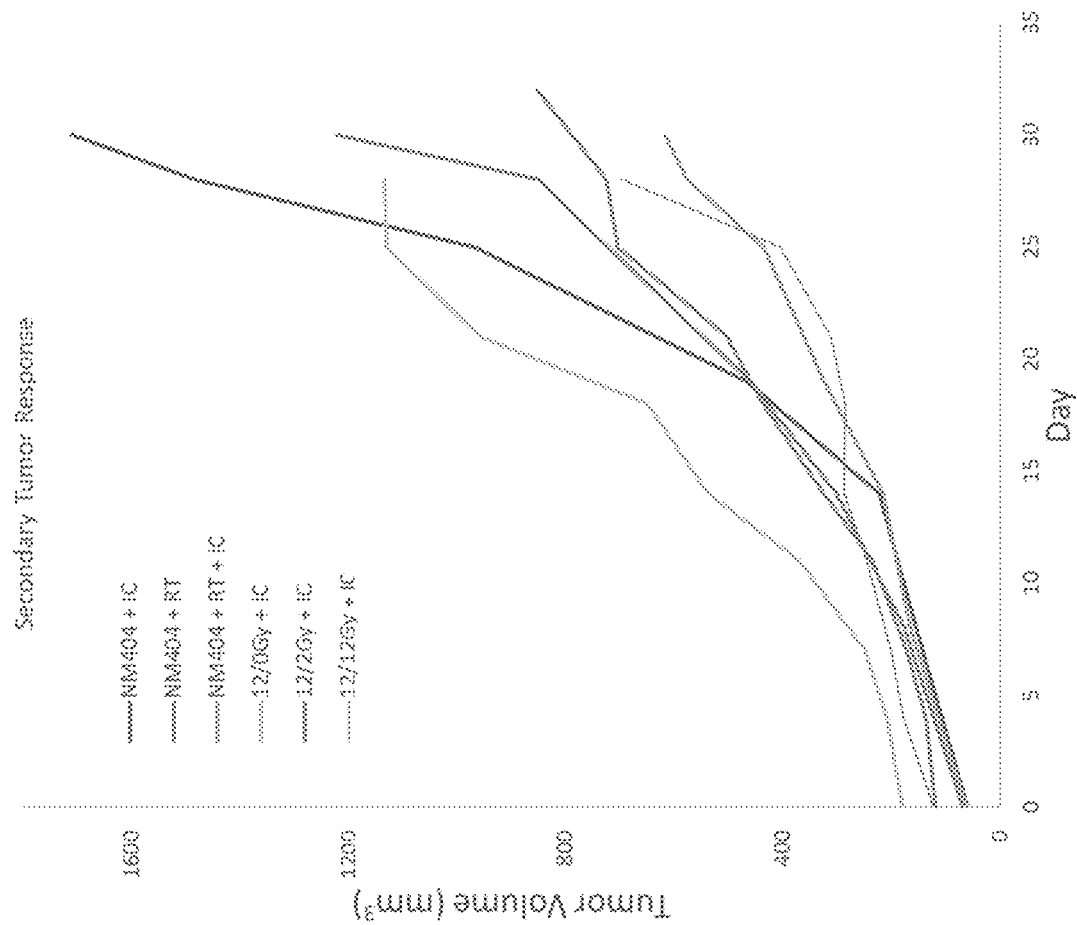

Given the capacity of low dose $^{131}$I-NM404 TRT to deplete tumor-infiltrating Tregs without rendering a mouse leukopenic, we tested whether low dose $^{131}$I-NM404 might effectively overcome concomitant immune tolerance. C57BL/6 mice bearing two B78 tumors were treated with 60-µCi $^{131}$I-NM404 on day 1 (NM404), as indicated. After one half-life (day 8), animals received 12 Gy xRT or no xRT to the primary tumor (in situ vaccine site). Control mice receiving no $^{131}$I-NM404 were treated to the secondary tumor as indicated (0, 2, or 12 Gy). Mice received daily IT injections of IC to the primary tumor (in situ vaccine site), as indicated, on days 13-17. Primary tumor (FIG. 12A) and secondary tumor (FIG. 12B) response demonstrates that administration of low dose TRT effectively overcomes concomitant immune tolerance and rescues the systemic anti-tumor effect of in situ vaccination.

Conclusion to the Examples

These examples illustrate a novel, never before tested or considered, anti-cancer strategy, based on the synergistic and widely applicable combination of two known therapeutic methods: (1) targeted systemic delivery of radiotherapy (J. Weichert and colleagues), and (2) local delivery of combined immunotherapy to induce an in situ cancer vaccine (P. Sondel and colleagues). As $^{131}$I-NM404 can target cancers of virtually any histology, and the local administration of anti-tumor mAb+IL2 could potentially be used for virtually any cancer type (since tumor reactive mAbs are approved or in clinical testing for nearly all cancer histological types), the clinical translation of the combined strategy will potentially result in clinically effective therapy for virtually all high risk cancers.

REFERENCES CITED IN THE EXAMPLES

[1] Hank J A, Robinson R R, Surfus J, Mueller B M, Reisfeld R A, Cheung N-K and Sondel P M. Augmentation of antibody dependent cell mediated cytotoxicity following in vivo therapy with recombinant Interleukin-2. Cancer Res. 50:5234-9. 1990.

[2] Neal Z C, Yang J C, Rakhmilevich A L, Buhtoiarov I, Lum H E, Imboden M, Hank J A, Lode H N, Reisfeld R A, Gillies S D, Sondel P M. Enhanced activity of hu14.18-IL2 IC against the murine NXS2 neuroblastoma when combined with IL2 therapy. Clin Cancer Res. 2004 Jul. 15; 10(14):4839-47.

[3] Yu A L, Gilman A L, Ozkaynak M F, London W B, Kreissman S, Chen H, Smith M, Anderson B, Villablanca J, Matthay K K, Shimada H, Grupp S A, Seeger R, Reynolds C P, Buxton A, Reisfeld R A, Gillies S D, Cohn S L, Maris J M, Sondel P M. Anti-GD2 antibody with GM-CSF, interleukin-2, and isotretinoin for neuroblastoma. N Engl J. Med. 2010 Sep. 30; 363(14):1324-34.

[4] Johnson E E, Yamane B H, Lum H D, Buhtoiarov I N, Rakhmilevich A L, Mahvi D M, Gillies S D, Sondel, P M.

Radiofrequency Ablation Combined with K S-IL2 IC (EMD 273066) Results in an Enhanced Anti-tumor Effect Against Murine Colon Adenocarcinoma. Clin Cancer Res. 2009 Aug. 1; 15(15):4875-84.

[5] Yang R K, Kalogriopoulos N A, Rakhmilevich A L, Ranheim E A, Seo S, Kim K M, Alderson K L, Gan J, Reisfeld R A, Gillies S D, Hank J A, Sondel P M. Intratumoral hu14.18-IL2 (IC) Induces Local and Systemic Antitumor Effects that Involve Both Activated T- and N K cells as well as Enhanced IC Retention. J Immunol. 2012 Sep. 1; 189(5):2656-64.

[6] Morris Z S, Emily I. Guy E I, Francis D M, Gressett M M, Carmichael L L, Yang R K, Armstrong E A, Huang S, Navid F, Gillies S D, Korman A, Hank J A, Rakhmilevich A L, Harari P M, Sondel P M. Combining Local Radiation and tumor-specific antibody or IC to elicit in situ tumor vaccination. Cancer Research, e-pub ahead of print, 2016.

[7] Morris Z S, G. E., Francis D M, Gressett M M, Armstrong E A, Huan S, Gillies S D, Korman A J, Hank J A, Rakhmilevich A L, Harari P M, and Sondel P M., IC augments local and abscopal response to radiation and CTLA-4 checkpoint inhibition in a murine melanoma model. Am. Soc. Therapeutic Radiation Oncology. Abstract accepted October 2015 (and selected as the meeting's winning abstract in the basic-translational science category).

[8] Weichert J P, Clark P A, Kandela I K, Vaccaro A M, Clarke W, Longino M A, Pinchuk A N, Farhoud M, Swanson K I, Floberg J M, Grudzinski J, Titz B, Traynor A M, Chen H E, Hall L T, Pazoles C J, Pickhardt P J, Kuo J S. Alkylphosphocholine Analogs for Broad Spectrum Cancer Imaging and Therapy. Science Translational Medicine 6, 240ra75, 1-10. 2014.

[9] Morris Z S, J P Weichert, J Sakera, E A Armstrong, A Besemer, B Bednarz, R Kimple, P M Harari. Therapeutic combination of radiolabeled NM404 with external beam radiation in head and neck cancer model systems. Radiotherapy and Oncology. J. Radiation Oncology, DOI. 10.1016. 2015.

[10] Lode H N, Xiang R, Dreier T, Varki N M, Gillies S D, Reisfeld R A. Natural killer cell-mediated eradication of neuroblastoma metastases to bone marrow by targeted interleukin-2 therapy. Blood 91(5), 1706-1715. 1998.

[11] Snyder F, Wood R. Alkyl and alk-1-enyl ethers of glycerol in lipids from normal and neoplastic human tissues. Cancer Res 29, 251-257. 1969.

[12] Pinchuk A N, Rampy M A, Longino M A, Skinner R W, Gross M D, Weichert J P, Counsell R E, Synthesis and structure-activity relationship effects on th tumor avidity of radioiodinated phospholipid ether analogues. J Med Chem 49, 2155-2165. 2006.

[13] Swanson K I, Clark P A, Pinchuk A N, Longino M A, Farhoud M, Weichert J P, Kuo J S. Initial Studies on Novel Cancer-Selective Alkylphosphocholine Analogs CLR1501 and CLR1502 for Fluorescence-guided Neurosurgery. Neurosurgery. 76(2): 115-123. 2015.

[14] Filatenkov A, Baker J, Mueller A M, Kenkel J, Ahn G O, Dutt S, Zhang N, Kohrt H, Jensen K, Dejbakhsh-Jones S, Shizuru J A, Negrin R N, Engleman E G, Strober S. Ablative Tumor Radiation Can Change the Tumor Immune Cell Microenvironment to Induce Durable Complete Remissions. Clin Cancer Res. 21:3727-39. 2015.

[15] Jing W, Gershan J A, Weber J, Tlomak D, McOlash L, Sabatos-Peyton C, Johnson B D. Combined immune checkpoint protein blockade and low dose whole body irradiation as immunotherapy for myeloma. J Immunother Cancer. 3:2. 2015.

[16] Bednarz B., Besemer A., Yang Y. A Monte Carlo-Based Small Animal Dosimetry Platform for Pre-Clinical Trials: Proof of Concept. Med. Phys. 39, 3899. 2012.

[17] Besemer et al. Towards Personalized Dosimetry Using Diapeutic Radiopharmaceuticals. Med. Phys. 40, 382. 2013.

[18] Besemer A. and Bednarz B. Validation of a patient-specific Monte Carlo targeted radionuclide therapy dosimetry platform. Med. Phys. 41, 303. 2014.

[19] Imboden M, Murphy K R, Rakhmilevich A L, Neal Z C, Xiang R, Reisfeld R A, Gillies S D and Sondel P M. The level of MHC Class I expression on murine adenocarcinoma can change the antitumor effector mechanism of immunocytokine therapy. Cancer Res. 61:1500-7. 2001.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

The invention claimed is:

1. A method of treating a metastatic cancer in a subject, wherein the metastatic cancer comprises a primary malignant solid tumor and one or more metastatic tumors capable of causing concomitant immune tolerance, the method comprising the steps of:

(a) administering to the subject an immunomodulatory dose of a radiohalogenated compound that is differentially taken up by and retained within malignant solid tumor tissue and comprises a metaiodobenzylguanidine (MIBG), wherein the iodine atom in the MIBG is a radioactive iodine isotope, or a phospholipid compound having the formula:

$$R_1-\phenyl_a-(CH_2)_n(OCH_2CHYCH_2)_m O\overset{O}{\underset{O^-}{\overset{\|}{P}}}OCH_2CH_2-R_2$$

or a salt thereof, wherein:

$R_1$ comprises a radioactive halogen isotope;

a is 0 or 1;

n is an integer from 12 to 30;

m is 0 or 1;

Y is selected from the group consisting of —H, —OH, —COOH, —COOX, —OX, and —OCOX, wherein X is an alkyl or an arylalkyl; and $R_2$ is selected from the group consisting of —$N^+H_3$, —$N^+H_2Z$, —$N^+HZ_2$, and —$N^+Z_3$, wherein each Z is independently an alkyl or an aryl; and (b) performing in situ tumor vaccination in the subject at the primary malignant solid tumor using one or more treatments capable of stimulating specific immune cells within the tumor microenvironment, wherein the one or more treatments capable of stimulating specific immune cells within the tumor microenvironment comprise contacting the primary malignant solid tumor with a composition comprising one or more agents capable of stimulating specific immune cells within the tumor microenvironment;

whereby the concomitant immune tolerance caused by the metastatic tumors is prevented and the metastatic cancer is treated in the subject.

2. The method of claim 1, wherein step (b) of performing in situ tumor vaccination in the subject further comprises treating the primary malignant solid tumor with external beam radiation therapy (xRT).

3. The method of claim 1, wherein the immunomodulatory dose of the radiohalogenated compound delivers a radiation dose of from 2 Gy to 8 Gy to the metastatic tumors.

4. The method of claim 1, wherein the one or more agents capable of stimulating specific immune cells within the tumor microenvironment are selected from the group consisting of an immunostimulatory mAb, a pattern recognition receptor agonist, an immunostimulatory cytokine, an immune stimulatory nanoparticle, an oncolytic virus, and combinations thereof.

5. The method of claim 4, wherein the immunostimulatory mAb is selected from the group consisting of an anti-GD2 antibody, an anti-CTLA-4 antibody, an anti-CD137 antibody, an anti-CD134 antibody, an anti-PD-I antibody, an anti-KIR antibody, an anti-LAG-3 antibody, an anti-PD-LI antibody, an anti-CD40 antibody, and combinations thereof.

6. The method of claim 4, wherein the immunostimulatory mAb is an antibody to a tumor-specific antigen.

7. The method of claim 5, wherein the immunostimulatory mAb is an anti-GD2 antibody.

8. The method of claim 7, wherein the composition comprising one or more agents capable of stimulating specific immune cells within the tumor microenvironment further comprises interleukin-2 (IL-2).

9. The method of claim 1, wherein the composition further comprises IL-2.

10. The method of claim 4, wherein the immunostimulatory cytokine is IL-2, interleukin-15 (IL-15), interleukin-21 (IL-21) interleukin-12 (IL-12), or an interferon.

11. The method of claim 4, wherein the pattern recognition receptor agonist is an agonist of a toll-like receptor (TLR).

12. The method of claim 1, wherein the radioactive iodine isotope is selected from the group consisting of $^{123}$I, $^{124}$I, $^{125}$I, and $^{131}$I.

13. The method of claim 1, wherein the radioactive halogen isotope is selected from the group consisting of $^{123}$I, $^{124}$I, $^{125}$I, $^{131}$I, and $^{211}$At.

14. The method of claim 13, wherein a is 1, m is 0, n is 18, and $R_2$ is —$N^+H_3$.

15. The method of claim 14, wherein the radiohalogenated compound is [$^{123}$I]—NM404, [$^{124}$I]—NM404, [$^{125}$I]—NM404 or [$^{131}$I]—NM404.

16. The method of claim 1, wherein the radiohalogenated compound is administered intravenously.

17. The method of claim 1, wherein the metastatic cancer that is treated is selected from the group consisting of melanoma, neuroblastoma, lung cancer, adrenal cancer, colon cancer, colorectal cancer, ovarian cancer, prostate cancer, liver cancer, subcutaneous cancer, squamous cell cancer of the skin or head and neck, intestinal cancer, retinoblastoma, cervical cancer, glioma, breast cancer, pancreatic cancer, soft tissue sarcomas, Ewings sarcoma, rhabdomyosarcoma, osteosarcoma, retinoblastoma, Wilms' tumor, and pediatric brain tumors.

18. The method of claim 1, wherein the step of contacting the primary malignant solid tumor with the composition is performed by intratumorally injecting the composition into the primary malignant solid tumor.

\* \* \* \* \*